US008226814B2

(12) United States Patent
Mao et al.

(10) Patent No.: US 8,226,814 B2
(45) Date of Patent: *Jul. 24, 2012

(54) TRANSITION METAL COMPLEXES WITH PYRIDYL-IMIDAZOLE LIGANDS

(75) Inventors: Fei Mao, Fremont, CA (US); Adam Heller, Austin, TX (US)

(73) Assignee: Abbott Diabetes Care Inc., Alameda, CA (US)

( * ) Notice: Subject to any disclaimer, the term of this patent is extended or adjusted under 35 U.S.C. 154(b) by 405 days.

This patent is subject to a terminal disclaimer.

(21) Appl. No.: 12/102,749

(22) Filed: Apr. 14, 2008

(65) Prior Publication Data

US 2009/0095642 A1 Apr. 16, 2009

Related U.S. Application Data

(63) Continuation-in-part of application No. 11/933,219, filed on Oct. 31, 2007, now Pat. No. 8,070,934, which is a continuation-in-part of application No. 11/361,427, filed on Feb. 24, 2006, now Pat. No. 7,465,796, which is a continuation of application No. 10/714,835, filed on Nov. 14, 2003, now Pat. No. 7,074,308, which is a continuation of application No. 10/143,300, filed on May 9, 2002, now Pat. No. 6,676,816.

(60) Provisional application No. 60/290,537, filed on May 11, 2001.

(51) Int. Cl.
*G01N 27/327* (2006.01)
(52) U.S. Cl. ................ 205/777.5; 204/403.02
(58) Field of Classification Search ............ 204/403.01, 204/403.04, 403.14; 205/777.5; 548/101; 546/2; 526/161
See application file for complete search history.

(56) References Cited

U.S. PATENT DOCUMENTS

| | | | |
|---|---|---|---|
| 4,382,872 A | 5/1983 | Grinstead | |
| 4,421,751 A | 12/1983 | Sundelin | |
| 5,236,567 A * | 8/1993 | Nanba et al. | 204/403.1 |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,320,725 A | 6/1994 | Gregg et al. | |
| 5,356,786 A | 10/1994 | Heller et al. | |
| 5,378,628 A | 1/1995 | Gratzel et al. | |
| 5,393,903 A | 2/1995 | Gratzel et al. | |
| 5,410,059 A | 4/1995 | Fraser et al. | |
| 5,437,999 A | 8/1995 | Diebold et al. | |
| 5,463,057 A | 10/1995 | Graetzel et al. | |
| 5,563,057 A | 10/1996 | Gellman et al. | |
| 5,589,326 A | 12/1996 | Deng et al. | |
| 5,593,852 A | 1/1997 | Heller et al. | |
| 5,665,222 A | 9/1997 | Heller et al. | |
| 5,683,832 A | 11/1997 | Bonhote et al. | |
| 5,789,592 A | 8/1998 | Gratzel et al. | |
| 5,804,049 A | 9/1998 | Chan | |
| 5,846,702 A | 12/1998 | Deng et al. | |
| 5,965,380 A | 10/1999 | Heller et al. | |
| 5,972,199 A | 10/1999 | Heller et al. | |
| 6,083,710 A | 7/2000 | Heller et al. | |
| 6,103,033 A | 8/2000 | Say et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,175,752 B1 | 1/2001 | Say et al. | |
| 6,245,988 B1 | 6/2001 | Gratzel et al. | |
| 6,262,264 B1 | 7/2001 | Buck, Jr. et al. | |
| 6,278,056 B1 | 8/2001 | Sugihara et al. | |
| 6,294,062 B1 | 9/2001 | Buck, Jr. et al. | |
| 6,338,790 B1 | 1/2002 | Feldman et al. | |
| 6,352,824 B1 | 3/2002 | Buck, Jr. et al. | |
| 6,605,200 B1 | 8/2003 | Mao et al. | |
| 6,605,201 B1 | 8/2003 | Mao et al. | |
| 6,616,819 B1 | 9/2003 | Liamos et al. | |
| 6,676,816 B2 | 1/2004 | Mao et al. | |
| 6,746,582 B2 | 6/2004 | Heller et al. | |
| 7,074,308 B2 | 7/2006 | Mao et al. | |
| 2003/0042137 A1 | 3/2003 | Mao et al. | |
| 2003/0077772 A1 | 4/2003 | Shah et al. | |
| 2003/0096997 A1* | 5/2003 | Mao et al. | 546/2 |
| 2004/0040840 A1 | 3/2004 | Mao et al. | |

(Continued)

FOREIGN PATENT DOCUMENTS

EP 1 230 249 B1 6/2004

(Continued)

OTHER PUBLICATIONS

Degani, Y. et al., Direct Electrical Communication between Chemically Modified Enzymes and Metal Electrodes. 1. Electron Transfer from Glucose Oxidase to Metal Electrodes via Electron Relays, Bound Covalently to the Enzyme, J. Phys. Chem., vol. 91, No. 6, pp. 1285-1289 (1987).

Buckingham, et al. "Osmium(III)-Osmium(II) Electrode Potentials. The Effects of Charge, Conjugation, Coordinated Halide, and Substitution in the Ligand" Inorganic Chemistry, 5(7):1243-1249 (1966).

Abruna et al., "Rectifying Interfaces Using Two-Layer Films of Electrochemically Polymerized Vinylpyrdine and Vinylbipyridine Complexes of Ruthenium and Iron on Electrodes," *J. Am. Chem. Soc.*, vol. 103. No. 1 pp. 1-5 (Jan. 14, 1981).

Calvert et al., "Synthetic and Mechanistic Investigations of the Reductive Electrochemical Polymerization of Vinyl-Containing Complexes of Iron (II), Ruthenium(II), and Osmium(II), "Inorganic Chemistry, vol. 22, No. 15, pp. 2151-2162 (1983).

(Continued)

*Primary Examiner* — Kaj K Olsen

(74) *Attorney, Agent, or Firm* — Edward J. Baba; Khin K. Chin; Bozicevic, Field & Francis LLP

(57) ABSTRACT

Enzyme-based electrochemical sensors comprising transition metal complexes of iron, cobalt, ruthenium, osmium, and vanadium are described. The transition metal complexes can be used as redox mediators and include substituted or unsubstituted pyridyl-imidazole ligands. Transition metal complexes attached to polymeric backbones are also described.

16 Claims, No Drawings

U.S. PATENT DOCUMENTS

2004/0074785 A1 4/2004 Holker et al.

FOREIGN PATENT DOCUMENTS

| WO | WO 98/35225 | 8/1998 |
| --- | --- | --- |
| WO | WO 99/03868 | 1/1999 |
| WO | WO 99/45375 | 9/1999 |
| WO | WO 99/45387 | 9/1999 |
| WO | WO 99/56613 | 11/1999 |
| WO | WO 99/59218 | 11/1999 |
| WO | WO 99/67628 | 12/1999 |
| WO | WO 00/20626 | 4/2000 |
| WO | WO 01/36430 | 5/2001 |
| WO | WO 01/36660 | 5/2001 |
| WO | WO 03/098731 | 11/2003 |

OTHER PUBLICATIONS

Cass et al., "Ferrocene-Mediated Enzyme Electrode for Amperometric Determination of Glucose," *Anal. Chem.* vol. 56, No. 4, pp. 667-671 (Apr. 1984).

Cass et al., "Ferricinum Ion as an Electron Acceptor for Oxido-Reductases," *Electroanal. Chem.*, vol. 190, pp. 117-127 (1985).

Chen et al., "A Biocompatible Needle-Type Glucose Sensor Based on Platinum-Electroplated Carbon Electrode," *Applied Biochemistry and Biotechnology*, vol. 36, pp. 211-226 (1992).

Chen et al., "Amperometric Needle-Type Glucose Sensor Based on a Modified Platinum Electrode with Diminished Response to Interfering Materials," *Analytica Chimica Acta*, vol. 265, pp. 5-14 (1992).

Chiswell et al., "Bidentate Chelate Compounds. III. Metal Complexes of Some Pyridyl-imidazole Derivatives" *Inorg. Chem.*, 3 (1), pp. 110-114 (1964).

Communication Pursuant to Article 96(2), European Patent Application No. 00 978 573.4-2117 for TheraSense, Inc. dated Dec. 2, 2003, 9 pages.

Communication Pursuant to Article 96(2), European Patent Application No. 00 978 573.4-2117 for TheraSense, Inc. dated May 31, 2005, 4 pages.

Csöregi et al, "Design, Characterization, and One-Point in Vivo Calibration of a Subcutaneously Implanted Glucose Electrode," *Anal. Chem.*, vol. 66, No. 19, pp. 3131-3138 (Oct. 1, 1994).

Csöregi et al, "On-Line Monitoring by Using Microdialysis Sampling and Amperometric Detection Based on 'Wired' Glucose Oxidase in Carbon Paste," *Mikrochim. Acta.*, vol. 121, pp. 31-40 (1995).

Degani et al., Direct Electrical Communication Between Chemically Modified Enzymes and Metal Electrodes. 1. Electron Transfer from Glucose Oxidase to Metal Electrodes via Electron Relays, Bound Covalently to the Enzyme. *J. Phys. Chem.* vol. 91, No. 6, pp. 1285-1289 (1987).

Degani et al., "Direct Electrical Communication Between Chemically Modified Enzymes and Metal Electrodes. 2. Methods for Bonding Electron-Transfer Relays to Glucose Oxidase and D-Amino-Acid Oxidase. " *J. Am. Chem. Soc.*, vol. 110, No. 8, pp. 2615-2620 (1988).

Degani et al., "Electrical Communication Between Redox Centers of Glucose Oxidase and Electrodes Via Electrostatically and Covalently Bound Redox Polymers:" *J. Am. Chem. Soc.*, vol. 111, pp. 2357-2358 (1989).

Dicks, "Ferrocene Modified Polypyrrole with Immobilised Glucose Oxidase and its Application in Amperometric Glucose Microbiosensors:" *Ann. Biol. Clin.*, vol. 47, pp. 607-619 (1989).

Doherty et al.: "The Effect of the Nature of the Polymer Backbone on he Stability and the Analytical Response of Polymer-Modified Electrodes," *Electroanalysis*, vol. 7, No. 4, pp. 333-339 (1995).

Fieselmann et al., "Synthesis, Electron Paramagnetic Resonance, and Magnetic Studies on Binuclear Resonance . . . ", *Inorganic Chemistry*, vol. 17, No. 8, pp. 2078-2084 (1978).

Fischer et al., "Intramolecular Electron Transfer Mediated by 4,4'-Bipyridine and Related Bridging Groups," *J. Am. Chem. Soc.*, vol. 98, No. 18, pp. 5512-5517 (Sep. 1, 1976).

Foulds et al., "Enzyme Entrapment in Electrically Conducting Polymers," *J. Chem. Soc., Faraday Trans 1.*, vol. 82, pp. 1259-1264 (1986).

Foulds et al., "Immobilization of Glucose Oxidase in Ferrocene-Modified Pyrrole Polymers," *Anal. Chem.*, vol. 60, No. 22, pp. 2473-2478 (Nov. 15, 1998).

Gholamkhass et al., "Evaluation of Electronic Interaction Matrix Elements for Photoinduced Electron Transfer Processes within Mixed-Valence Complexes," *J. Phys. Chem*, vol. 101, pp. 9010-9021 (1997).

Gregg et al., "Cross-Linked Redox Gels Containing Glucose Oxidase for Amperometric Biosensor Applications," *Analytical Chemistry*, vol. 62, No. 3, pp. 258-263 (Feb. 1, 1990).

Gregg et al., "Redox Polymer Films Containing Enzymes. 1. A Redox-Conducting Epoxy Cement: Synthesis, Characterization, and Electrocatalytic Oxidation of Hydroquinone," *J. Phys. Chem.*, vol. 95, No. 15, pp. 5970-5975 (1991).

Haga, "Synthesis and Protonation-Deprotanation Reactions of Ruthenium(II) Complexes Containing 2,2'—Bibenzimidazole and Related Ligands," *Inorganica Chimica Acta*, vol. 75, pp. 29-35 (1983).

Hale et al., "A New Class of Amperometric Biosensor Incorporating a Polymeric Electron-Transfer Mediator," *J. Am. Chem. Soc.*, vol. 111, No. 9, pp. 3482-3484 (1989).

Heller et al., "Electrical Connection of Enzyme Redox Centers to Electrodes," *J. Phys. Chem.*, vol. 96, No. 9, pp. 3579-3587 (1992).

Heller, "Electrical Wiring of Redox Enzymes," *Acc. Chem. Res.*, vol. 23, No. 5, pp. 129-134 (1990).

Ianniello et al., "Immobilized Enzyme Chemically Modified Electrode as an Amperometric Sensor," *Anal. Chem.*, vol. 53, No. 13, pp. 2090-2095 (Nov. 1981).

Ikeda et al., "Glucose Oxidase-Immobilized Benzoquinone-Carbon Paste Electrode as a Glucose Sensor:" *Agric. Biol. Chem.*, vol. 49, No. 2, (1 page—Abstract only) (1985).

Jönsson et al.: "An Amperometric Glucose Sensor Made by Modifiction of a Graphite Electrode Surface with Immobilized Glucose Oxidase and Adsorbed Mediator:" *Biosensors*, vol. 1, pp. 355-368 (1985).

Katakis et al., "L-α-Glycerophosphate and L-Lactate Electrodes Based on the Electrochemical 'Wiring' of Oxidases," *Analytical Chemistry*, vol. 64, No. 9, pp. 1008-1013 (May 1, 1992).

Katakis et al., "Electrostatic Control of the Electron Transfer Enabling Binding of Recombinant Glucose Oxidase and Redox Polyelectrolytes," *J. Am. Chem. Soc.*, vol. 116. No. 8, pp. 3617-3618 (1994).

Kenausis et al., "'Wiring' of Glucose Oxidase and Lactate Oxidase Within a Hydrogel Made with Poly(Vinyl Pyridine) . . . " *J. Chem. Soc., Faraday Trans.*, vol. 92, No. 20, pp. 4131-4136 (1996).

Maidan et al., "Elimination of Electrooxidizable Interferant-Produced Currents in Amperometric Biosensors," *Analytical Chemistry*, vol. 64, No. 23, pp. 2889-2896 (Dec. 1, 1992).

Majumdar et al., "Biimidazole Complexes of ML22+[M=Ru or L=2-(Phenylazo)-Pyridine]. Synthesis, Structure and Redox Properties of Mono- and Di-Nuclear Complexes," *J. Chem. Soc. Dalton Trans.*, pp. 1569-1574 (1998).

OHara et al., "'Wired' Enzyme Electrodes for Amperometric Determination of Glucose or Lactate in the Presence of Interfering Substances," *Analytical Chemistry*, vol. 66, No. 15, pp. 2451-2457 (Aug. 1, 1994).

OHara, "Osmium Bipyridyl Redox Polymers Used in Enzyme Electrodes," *Platinum Metals Rev.*, vol. 39, No. 2, pp. 54-62 (Apr. 1995).

OHara et al., "Glucose Electrodes Based on Cross-Linked $[Os(bpy)_2Cl]^{+/2+}$ Complexed Poly(1-vinylimadazole) Films," *Analytical Chemistry*, vol. 65, No. 23, pp. 3512-3516 (Dec. 1, 1993).

OHara et al., "Glucose Electrodes Based on Cross-Linked $[Os(bpy)_2Cl]^{+/2+}$ Complexed Poly(1—vinylimadazole) Films," Department of Chemical Engineering University of Texas at Austin, pp. 182-183, Polym. Mater. Sci. Eng., vol. 70, 1993.

Pickup, J. "Potentially-Implantable, Amperometric Glucose Sensors with Mediated Electron Transfer: Improving the Operating Stability," *Biosensors*, vol. 4, No. 2, (1 page—Abstract only) (1989).

Pishko et al., "Amperometric Glucose Microelectrodes Prepared Through Immobilization of Glucose Oxidase in Redox Hydrogels," *Anal. Chem.*, vol. 63, No. 20, pp. 2268-2272 (Oct. 15, 1991).

Pollak et al., "Enzyme Immobilization by Condensation Copolymerization into Cross-Linked Polyacrylamide Gels," *J. Am. Chem. Soc.*, vol. 102, No. 20, pp. 6324-6336 (1980).

Reeder et al., "Solution-State Spin-Equilibrium Properties of the Tris[2-(2-Pyridyl)imidazole]iron(II) and Tris[2-92-Pyridyl)benzimidazole]iron(II) Cations," *Inorganic Chemistry*, vol. 17, No. 4, pp. 1071-1075 (1978).

Sasso et al., "Electropolymerized 1,2-Diaminobenzene as a Means to Prevent Interferences and Fouling and to Stabilize Immobilized Enzyme in Electrochemical Biosensors," *Anal. Chem.*, vol. 62, No. 11, pp. 1111-1 117 (Jun. 1, 1990).

Schalkhammer et al., "Electrochemical Glucose Sensors on Permselective Non-Conducting Substituted Pyrrole Polymers:" *Sensors and Actuators*, vol. 84, pp. 273-281 (1991).

Schmehl et al., "The Effect of Redox Site Concentration on the Rate of Mediated Oxidation of Solution Substrates by a Redox Copolymer Film, "*Journal of Electroanalytical Chemistry*, vol. 152, pp. 97-109 (1983).

Surridge et al., Electron and Counterion Diffusion Constants in Mixed-Valent Polymeric Osmium Bipyridine Films, *The Journal of Physical Chemistry*, vol. 98, No. 3, pp. 917-923 (1994).

Surridge et al., "Site Dilution of Osmium Polypyridine Complexes in Three Electron-Hopping Conductive Polymer Films on Electrodes by Electrochemical Copolymerization of Osmium with Ruthenium and with Zinc Complexes," *Inorganic Chemistry*, vol. 29, No. 24, pp. 4950-4955 (1990).

Taylor et al., "'Wiring' of Glucose Oxidase Within a Hydrogel Made with Polyvinyl Imidazole Complexed with [(Os-4,4'-Dimethoxy-2,2'-Bipyridine)C1]$^{+/2+}$," *Journal of Electroanalytical Chemistry*, vol. 396, pp. 511-515 (1995).

Trojanowicz t al., "Enzyme Entrapped Polypyrrole Modified Electrode for Flow-Injection Determination of Glucose," *Biosensors & Bioelectronics*, vol. 5, pp. 149-156 (1990).

Ye et al.: "High Current Density 'Wired' Quinoprotein Glucose Dehydrogenase Electrode," *Anal. Chem.*, vol. 65, No. 3, pp. 238-241 (Feb. 1, 1993).

Yildiz et al., "Evaluation of an Improved Thin-Layer Electrode," *Analytical Chemistry*, vol. 40, No. 7, pp. 1018-1024 (Jun. 1968).

Yu et al.,"Synthesis, Metal Complex Formation, and Electronic Properties of a Novel Conjugate Polymer with a Tridentate 2,6-Bis(benzimidazol-2-yl)pyridine Ligand," *Macromolecules*, vol. 32, pp. 5251-5256 (1999).

\* cited by examiner

US 8,226,814 B2

TRANSITION METAL COMPLEXES WITH PYRIDYL-IMIDAZOLE LIGANDS

CROSS-REFERENCE TO RELATED APPLICATIONS

This application is a continuation-in-part of prior filed U.S. patent application Ser. No. 11/933,219, filed Oct. 31, 2007, now U.S. Pat. No. 8,070,934 and published as U.S. Patent Publication No. 2008/0197026 which is a continuation-in-part of U.S. patent application Ser. No. 11/361,427, filed Feb. 24, 2006, now U.S. Pat. No. 7,465,796, which is a continuation of U.S. patent application Ser. No. 10/714,835, filed Nov. 14, 2003, now U.S. Pat. No. 7,074,308, which is a continuation of U.S. patent application Ser. No. 10/143,300, filed May 9, 2002, now U.S. Pat. No. 6,676,816, and claims the benefit of priority of prior filed U.S. Provisional Patent Application No. 60/290,537, filed May 11, 2001. Each of the foregoing applications and patents is incorporated by reference herein in its entirety. This application controls to the extent there is any conflict with the above applications.

FIELD OF THE INVENTION

This invention relates to enzyme-based electrochemical sensors comprising transition metal complexes with pyridyl-imidazole ligands, which show improved response times in the detection and quantification of fluid analytes. The invention also relates to the preparation of transition metal complexes, which may be coordination complexes comprising osmium, and to the use of the transition metal complexes as redox mediators.

BACKGROUND OF THE INVENTION

Enzyme-based electrochemical sensors are widely used in the detection and measurement of analytes in clinical, environmental, agricultural and biotechnological applications. Analytes that can be measured in clinical assays of fluids of the human body include, for example, glucose, lactate, cholesterol, bilirubin and amino acids. Levels of these analytes in biological fluids, such as blood, are important for the diagnosis and the monitoring of diseases, such as diabetes mellitus, a disorder of the pancreas where insufficient production of insulin prevents normal regulation of blood sugar levels.

Small volume (e.g., less than 0.5 microliter), in vitro, electrochemical sensors are used with FREESTYLE® and FREESTYLE FLASH® glucose meters strips manufactured by Abbott Diabetes Care Inc., Alameda, Calif., USA. These test strip sensors generally include a working electrode on a first substrate, a counter (or counter/reference) electrode on a second substrate, and a sample chamber. The sample chamber is configured so that when a sample (e.g., of blood) is provided in the chamber, the sample is in electrolytic contact with both the working electrode, the counter electrode and any reference electrodes or indicator electrodes that may be present. This allows electrical current to flow between the electrodes to effect the electrolysis (electrooxidation or electroreduction) of the analyte. A spacer is generally positioned between first substrate and second substrate to provide a spacing between electrodes and to provide the sample chamber in which the sample is to be evaluated is housed.

The electrode system (carbon, gold, platinum, etc.) is laid on an insulating substrate surmounted by a reagent layer containing at least a redox enzyme/cofactor (GDH/NAD, HBDH/NAD, GOx/FAD, GDH/PQQ, GDH/FAD) which acts on an analyte (glucose, 3-hydroxybutyrate, etc.) and a redox mediator which provides electrical communication between the enzyme/cofactor and the electrode. The action of enzyme/cofactor on the analyte results in the conversion of oxidized mediator to its reduced form which, in turn, is oxidized at an electrode. This generates an electrical signal which is proportional to the analyte concentration. The enzyme is specific to the analyte to be detected, or to a product of the analyte. The turnover rate of the enzyme is typically related (preferably, but not necessarily, linearly) to the concentration of the analyte itself, or to its product, in the test solution.

The first generation of electrochemical biosensors used oxygen as the electron acceptor. Oxygen, however, becomes a limiting factor in the enzymatic reaction at high substrate concentrations due to its limited solubility in liquid. This limits the upper linear range of the oxidase-based biosensors. In order to overcome problems associated with insufficient oxygen concentration, a second generation of biosensors was developed that used electron or "redox" mediators as substitutes for oxygen. Such electron mediators, also referred to as "transition metal complexes" are redox chemicals capable of mediating the electron transfer in the regeneration of the enzyme to the active form. In some cases the transition metal complexes are coordination complexes comprising osmium, for example. The linear range of the resulting biosensors was significantly improved.

A redox mediator assists in the electrical communication between the working electrode and the enzyme. The redox mediator can be dissolved in the fluid to be analyzed, which is in electrolytic contact with the electrodes, or can be applied within a coating on the working electrode in electrolytic contact with the analyzed solution. The coating is preferably not soluble in water, though it may swell in water. Useful devices can be made, for example, by coating an electrode with a film that includes a redox mediator and an enzyme where the enzyme is catalytically specific to the desired analyte, or its product. In contrast to a coated redox mediator, a diffusional redox mediator, which can be soluble or insoluble in water, functions by shuttling electrons between, for example, the enzyme and the electrode. In any case, when the substrate of the enzyme is electrooxidized, the redox mediator transports electrons from the substrate-reduced enzyme to the electrode; and when the substrate is electroreduced, the redox mediator transports electrons from the electrode to the substrate-oxidized enzyme.

Recent enzyme-based electrochemical sensors have employed a number of different redox mediators such as monomeric ferrocenes, quinoid compounds including quinines (e.g., benzoquinones), nickel cyclamates, and ruthenium amines. For the most part, these redox mediators have one or more of the following limitations: the solubility of the redox mediators in the test solutions is low, their chemical, light, thermal, and/or pH stability is poor, or they do not exchange electrons rapidly enough with the enzyme or the electrode or both. Some mediators with advantageous properties are difficult to synthesize. Additionally, the redox potentials of some of these reported redox mediators are so oxidizing that at the potential at which the reduced mediator is electrooxidized on the electrode, solution components other than the analyte are also electrooxidized. Some other of these reported redox mediators are so reducing that solution components, such as, for example, dissolved oxygen, are also rapidly electroreduced. As a result, the sensor utilizing the mediator is not sufficiently specific.

Accordingly, although the mediator/oxidase-based biosensors eliminate the dependence on the oxygen concentration for the extended linear range of the sensor, oxygen-related drawbacks still exist. For example, some mediators are not as efficient at shuttling electrons with the enzyme as the oxygen molecule. And, any oxygen in the sample solution can effectively compete for the enzyme site. Thus, mediator/oxidase-based biosensors may generate inaccuracies resulting from different oxygen concentrations. This becomes more serious when the substrate concentration is at a low concentration level (e.g., glucose concentration less than 70 mg/dL).

To obviate the interference resulting from the varying oxygen concentration or so-called "oxygen effect" described above using the mediator/oxidase-based biosensors, an oxygen-insensitive enzyme such as glucose dehydrogenase (GDH) was used to replace the oxygen-sensitive oxidase such as glucose oxidase. Flavin adenine dinucleotide (FAD) and pyrroloquinoline quinone (PQQ) are redox coenzymes (also referred to as "co-factors") that act as prosthetic groups, which are involved in catalyzing reactions that generate electrons from the oxidation of glucose and other sugars. Glucose dehydrogenase, whose coenzyme can be PQQ or FAD, does not interact with oxygen. Therefore, the resultant glucose sensor is unaffected by variable oxygen concentration in the sample. Such a sensor may be in the form of a strip-commonly referred to as a test strip or sensor strip, e.g., analogous to FREESTYLE® strips manufactured by Abbott Diabetes Care Inc., Alameda, Calif., USA. FREESTYLE® is a product that has been developed and marketed using glucose dehydrogenase.

The use of glucose dehydrogenase overcomes the problems associated with the oxygen effect. Glucose dehydrogenase, however, is not as specific as glucose oxidase. Glucose dehydrogenase reacts not only with glucose but with sugars that are structurally similar to glucose such as galactose and maltose. Maltose is composed of two glucose units and galactose differs in structure from glucose only in the position of the hydroxyl group on carbon number 4; accordingly, significant interference may be expected. Indeed, glucose dehydrogenase-based biosensors are sensitive to maltose and have difficulty discriminating between glucose and galactose. Cross-reactivity with maltose is particularly important due to the use of icodextrin in peritoneal dialysis, which metabolizes to maltose in vivo. If a glucose monitor or test strip uses a glucose dehydrogenase pyrroloquinolinequinone method (PQQ-GDH), a falsely high glucose reading may be obtained, potentially causing over-administration of insulin to a subject, thereby unnecessarily lowering blood glucose levels. Such a lowering of blood glucose levels may cause serious reactions in patients such as, but not limited to, loss of consciousness.

Responding to the need for a glucose biosensor that does not "cross-react" with unintended analytes, and which can be used safely with peritoneal dialysis patients, FAD-GDH has replaced PQQ-GDH in some systems described herein. Unlike PQQ-GDH, FAD-GDH does not catalyze reactions that generate electrons from maltose or galactose. It is therefore a desirable choice as the coenzyme for use with glucose dehydrogenase.

The FAD-GDH enzyme system, however, performs ineffectively with certain mediators. The mediator known as "nPBI" having an n-pentylbenzimidazole ligand, shown below, for example, does not compete favorably for electrons from the enzyme when FAD is used in concert with glucose dehydrogenase.

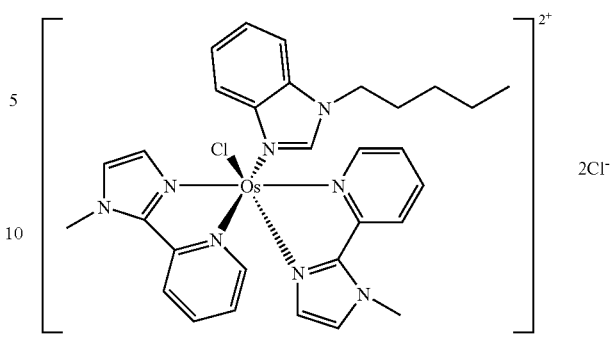

Redox Mediator $Os(MPI)_2(nPBI)Cl_3$ ("nPBI") −125 mV bis[4,4'-dimethoxy-2,2'-bipyridine-κN,N')] chloro(3-methylimidazole-κN$^3$)osmium(2+) dichloride Accordingly, there is a further need in the art for the synthesis of new redox mediators that perform effectively with the FAD-GDH enzyme system.

SUMMARY

The claimed subject matter is directed to enzyme-based electrochemical sensors comprising transition metal complexes with pyridyl-imidazole ligands, which show improved response times in the detection and quantification of fluid analytes. The claimed subject matter is also directed to the use of the complexes as redox mediators. The preferred redox mediators typically exchange electrons rapidly with enzyme:co-factor complexes and electrodes, are stable, can be readily synthesized, and have a redox potential that is tailored for the electrooxidation of analytes, such as glucose, for example.

Embodiments of the claimed subject matter include a sensor, for use in detecting the concentration of an analyte in a sample, comprising:
 (a) a first electrode, the first electrode being a working electrode; and
 (b) a second electrode, the second electrode being a reference electrode;
 wherein the first electrode comprises a reagent layer deposited thereon, the reagent layer comprising:
  (i) a coordination complex comprising osmium; and
  (ii) a dehydrogenase;
 wherein the coordination complex comprising osmium facilitates an electro-chemical connection between the working electrode and electrons generated from a reaction promoted by the enzyme with a target analyte to be detected and quantified, the coordination complex comprising osmium being characterized by transferring a detectable flow of electrons to the working electrode.

In some embodiments the dehydrogenase is a PQQ-dependent dehydrogenase. In some embodiments the dehydrogenase is a FAD-dependent dehydrogenase. In some embodiments the dehydrogenase is an NAD-dependent dehydrogenase. In some embodiments the analyte is selected from the group consisting of glucose, ketone bodies, cholesterol and lactate.

In some embodiments, the coordination complex comprising osmium is substantially non-reactive with reactants other than those involved in the transfer of electrons to the working electrode.

In a further embodiment, the coordination complex comprising osmium has a solubility of greater than 0.1 moles/Liter at 25° C. in an aqueous solvent.

In a further embodiment, the coordination complex comprising osmium has a redox potential ($E_{1/2}$ (mV)) versus the reference electrode of less than −70.

In a further aspect, the coordination complex comprising osmium has the following structural formula:

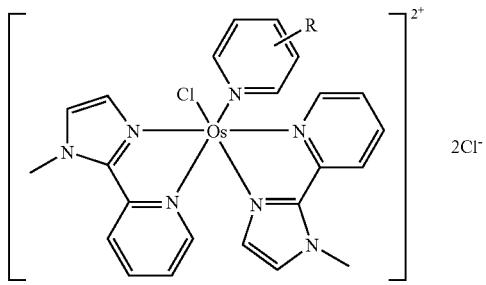

wherein R=$NHCH_3$, $N(CH_3)_2$, $OCH_3$, or OH, and may be attached at any position (ortho, meta, para) on the pyridine ring.

In a yet another embodiment, the coordination complex comprising osmium has the following formula:

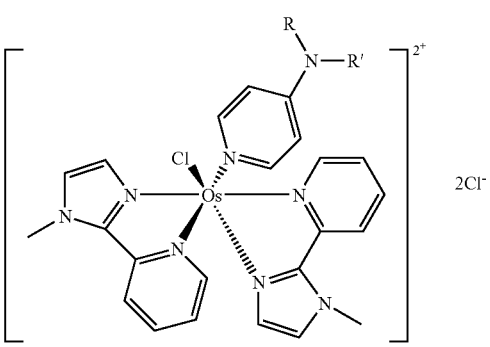

wherein each of R and R' may independently be —H or alkyl.

In a yet another embodiment, the coordination complex comprising osmium has the following formula:

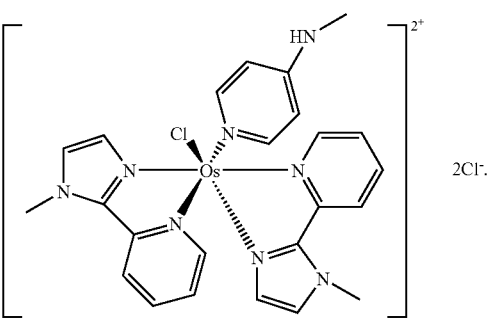

In a yet another embodiment, the coordination complex comprising osmium has the following formula:

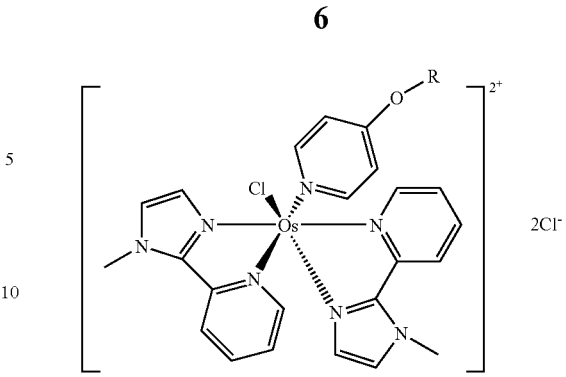

wherein R is —H or alkyl.

Embodiments of the claimed subject matter may also include an electrode coated with a reagent, the reagent comprising:
(a) a coordination complex comprising osmium; and
(b) an enzyme:co-factor system;
(i) wherein the coordination complex comprising osmium facilitates an electrochemical connection between the working electrode and electrons generated by a reaction promoted by the enzyme with a target analyte to be detected and quantified, the coordination complex comprising osmium being characterized by transferring a detectable flow of electrons to the working electrode; and
(ii) wherein the enzyme:co-factor system comprises a dehydrogenase.

In some embodiments the dehydrogenase is a PQQ-dependent dehydrogenase. In some embodiments the dehydrogenase is a FAD-dependent dehydrogenase. In some embodiments the dehydrogenase is an NAD-dependent dehydrogenase. In some embodiments the analyte is selected from the group consisting of glucose, ketone bodies, cholesterol and lactate.

In some embodiments, for example, the coordination complex comprising osmium may have the following formula:

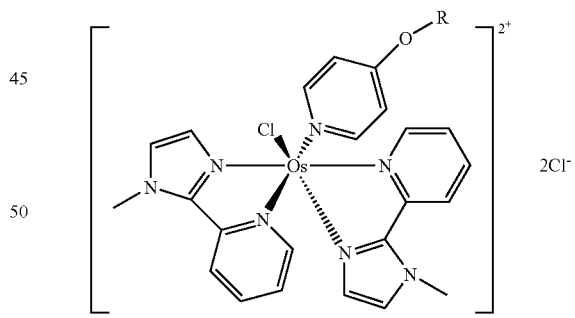

wherein R is —H or alkyl.

Embodiments of the claimed subject matter may also include a method of determining glucose concentration, comprising the steps of:
(a) contacting a body fluid comprising glucose with a sensor comprised of an electrode, a coordination complex comprising osmium and FAD-glucose dehydrogenase;
(b) allowing electrons generated as a result of a reaction catalyzed by FAD-glucose dehydrogenase to flow to the electrode via the coordination complex comprising osmium to thereby generate an electrical signal proportionally related to the glucose concentration in the body fluid.

In some embodiments, for example, the coordination complex comprising osmium of the methods described herein has the following formula:

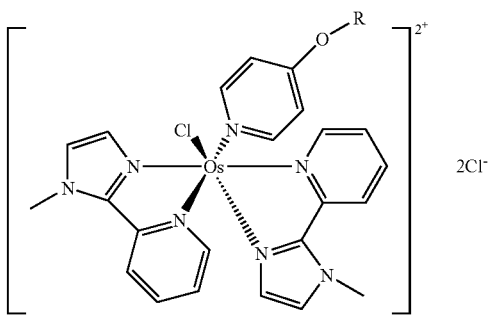

wherein R is —H or alkyl.

An embodiment of the invention is also a transition metal complex having the general formula set forth below.

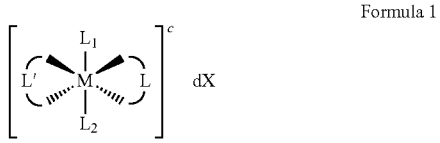

Formula 1

In this general formula, M is cobalt, iron, ruthenium, osmium, or vanadium; c is an integer representing the valence and is selected from +1 to +5 indicating a positive charge; X represents at least one counter ion having a charge opposite of c; d is an integer from 1 to 5 representing the number of counter ions, $L_1$ and $L_2$ are independent ligands and L and L' are independent and are represented by Formula 2 below:

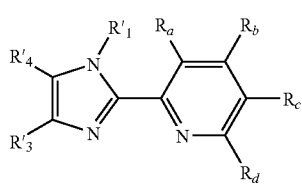

Formula 2 wherein $R'_1$ is a substituted or an unsubstituted alkyl, alkenyl, or aryl group. The variables $R'_3$, $R'_4$, $R_a$, $R_b$, $R_c$, and $R_d$ are independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl.

Here and throughout the description and claims, the symbols ⁄ and ⁀ are used to show a particular three-dimensional conformation. Those skilled in the art will understand that each ⁄ can be ⁀ and each ⁀ can be ⁄ so that the structures shown cover all possible isomers unless specifically indicated as being limited to a particular configuration.

Throughout the specification and the appended claims, a given chemical formula or name shall encompass all stereo and optical isomers and racemates thereof as well as mixtures in different proportions of the separate enantiomers, where such isomers and enantiomers exist, as well as pharmaceutically acceptable salts thereof. Isomers may be separated using conventional techniques, e.g. chromatography or fractional crystallisation. The enantiomers may be isolated by separation of racemate for example by fractional crystallisation, resolution or HPLC. The diastereomers may be isolated by separation of isomer mixtures for instance by fractional crystallisation, HPLC or flash chromatography. Alternatively the stereoisomers may be made by chiral synthesis from chiral starting materials under conditions which will not cause racemisation or epimerisation, or by derivatisation, with a chiral reagent. All stereoisomers are included within the scope of the invention.

Certain compounds of the present invention may exist as tautomers. It is to be understood that the present invention encompasses all such tautomers.

The transition metal complexes of the present invention are effectively employed as redox mediators in electrochemical sensors, given their very fast kinetics. More particularly, when a transition metal complex of this invention is so employed, rapid electron exchange between the transition metal complex and the enzyme and/or the working electrode in the sensor device occurs. This electron exchange is sufficiently rapid to facilitate the transfer of electrons to the working electrode that might otherwise be transferred to another electron scavenger in the system. The fast kinetics of the mediator is generally enhanced when $L_2$ of a mediator of the formula provided above is a negatively charged ligand.

The transition metal complexes of the present invention are also quite stable. For example, when such a complex is used as a mediator in an electrochemical sensor, the chemical stability is generally such that the predominant reactions in which the mediator participates are the electron-transfer reaction between the mediator and the enzyme and the electrochemical redox reaction at the working electrode. The chemical stability may be enhanced when a mediator of the formula provided above, wherein $L_1$ is a negatively charged ligand, has a "bulky" chemical ligand, $L_1$, that shields the redox center, M, and thereby reduces undesirable chemical reactivity beyond the desired electrochemical activity.

The electrochemical stability of the transition metal complexes of the present invention is also quite desirable. For example, when such a complex is used as a mediator in an electrochemical sensor, the mediator is able to operate in a range of redox potentials at which electrochemical activity of common interfering species is minimized and good kinetic activity of the mediator is maintained.

Thus, the claimed subject matter provides enzyme-based electrochemical sensors comprising transition metal complexes with pyridyl-imidazole ligands, which show improved response times in the detection and quantification of fluid analytes. The claimed subject matter is also directed to the use of the complexes as redox mediators. The advantageous properties and characteristics of said transition metal complexes make them ideal candidates for use in the electrochemical sensing of glucose, an application of particular importance in the treatment of diabetes in human populations.

DETAILED DESCRIPTION

Generally, the present invention relates to enzyme-based electrochemical sensors comprising transition metal complexes of iron, cobalt, ruthenium, osmium, and vanadium. The invention also relates to the preparation of the transition metal complexes and to the use of the transition metal complexes as redox mediators. In at least some instances, the transition metal complexes have one or more of the following characteristics: redox potentials in a particular range, the ability to exchange electrons rapidly with electrodes, the ability to rapidly transfer electrons to or rapidly accept electrons from an enzyme to accelerate the kinetics of electrooxidation or electroreduction of an analyte in the presence of an enzyme or another analyte-specific redox catalyst. In some cases, the transition metal complex may be described as a coordination complex comprising osmium.

For example, a redox mediator may accelerate the electrooxidation of glucose in the presence of glucose oxidase, FAD-glucose dehydrogenase or PQQ-glucose dehydrogenase, a process that can be useful for the selective assay of glucose in the presence of other electrochemically oxidizable species. Some embodiments of the invention may be easier or more cost-effective to make synthetically, or more cost-effective reagents in synthesis than other transition metal redox mediators.

When used herein, the definitions set forth below in quotations define the stated term.

The term "alkyl" includes linear or branched, saturated aliphatic hydrocarbons. Examples of alkyl groups include methyl, ethyl, n-propyl, isopropyl, n-butyl, tert-butyl and the like. Unless otherwise noted, the term "alkyl" includes both alkyl and cycloalkyl groups.

The term "alkoxy" describes an alkyl group joined to the remainder of the structure by an oxygen atom. Examples of alkoxy groups include methoxy, ethoxy, n-propoxy, isopropoxy, butoxy, tert-butoxy, and the like. In addition, unless otherwise noted, the term 'alkoxy' includes both alkoxy and cycloalkoxy groups.

The term "alkenyl" describes an unsaturated, linear or branched aliphatic hydrocarbon having at least one carbon-carbon double bond. Examples of alkenyl groups include ethenyl, 1-propenyl, 2-propenyl, 1-butenyl, 2-methyl-1-propenyl, and the like.

A "reactive group" is a functional group of a molecule that is capable of reacting with another compound to couple at least a portion of that other compound to the molecule. Reactive groups include carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxylamine, alkyl halide, imidazole, pyridine, phenol, alkyl sulfonate, halotriazine, imido ester, maleimide, hydrazide, hydroxy, and photo-reactive azido aryl groups. Activated esters, as understood in the art, generally include esters of succinimidyl, benzotriazolyl, or aryl substituted by electron-withdrawing groups such as sulfo, nitro, cyano, or halo groups; or carboxylic acids activated by carbodiimides.

A "substituted" functional group (e.g., substituted alkyl, alkenyl, or alkoxy group) includes at least one substituent selected from the following: halogen, alkoxy, mercapto, aryl, alkoxycarbonyl, alkylaminocarbonyl, dialkylaminocarbonyl, —OH, —NH$_2$, alkylamino, dialkylamino, trialkylammonium, alkanoylamino, arylcarboxamido, hydrazino, alkylthio, alkenyl, and reactive groups.

A "biological fluid" is any body fluid or body fluid derivative in which the analyte can be measured, for example, blood, interstitial fluid, plasma, dermal fluid, sweat, and tears.

An "electrochemical sensor" is a device configured to detect the presence of or measure the concentration or amount of an analyte in a sample via electrochemical oxidation or reduction reactions. These reactions typically can be transduced to an electrical signal that can be correlated to an amount or concentration of analyte.

A "redox mediator" is an electron transfer agent for carrying electrons between an analyte or an analyte-reduced or analyte-oxidized enzyme and an electrode, either directly, or via one or more additional electron transfer agents. Redox mediators that include a polymeric backbone may also be referred to as "redox polymers". An example of a redox mediator of the invention is a coordination complex comprising osmium.

"Electrolysis" is the electrooxidation or electroreduction of a compound either directly at an electrode or via one or more electron transfer agents (e.g., redox mediators or enzymes).

The term "reference electrode" includes both a) reference electrodes and b) reference electrodes that also function as counter electrodes (i.e., counter/reference electrodes), unless otherwise indicated.

The term "counter electrode" includes both a) counter electrodes and b) counter electrodes that also function as reference electrodes (i.e., counter/reference electrodes), unless otherwise indicated.

"Ketone bodies" refer to water-soluble compounds that are produced as by-products when fatty acids are broken down for energy in the liver and kidney. Ketone bodies may be used as a source of energy in the heart and brain. Examples of ketone bodies include acetone, acetoacetic acid, and beta-hydroxybutyric acid, with beta-hydroxybutyric acid also being a carboxylic acid.

Compounds having Formula 1, set forth below, are examples of transition metal complexes of the present invention.

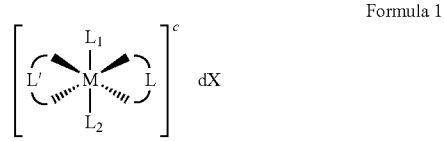

Formula 1

M is a transition metal and is typically iron, cobalt, ruthenium, osmium, or vanadium. Ruthenium and osmium are particularly suitable for redox mediators. L and L' are each bidentate, substituted or unsubstituted 2-(2-pyridyl)imidazole ligands having the Structure 2 set forth below.

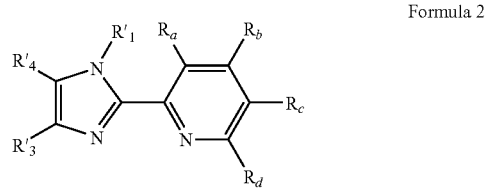

Formula 2

In Formula 2, R'$_1$ is a substituted or an unsubstituted aryl, alkenyl, or alkyl. Generally, R'$_1$ is a substituted or an unsubstituted C1-C12 alkyl or alkenyl, or an aryl, such as phenyl, optionally substituted with a substituent selected from a group consisting of —Cl, —F, —CN, amino, carboxy, C1-C6 alkyl, C1-C6 alkylthio, C1-C6 alkylamino, C1-C6 dialkylamino, C1-C6 alkylaminocarbonyl, C1-C6 alkoxy, C1-C6 alkoxycarbonyl, and C1-C6 alkylcarboxamido. R'1 is typically methyl or a C1-C12 alkyl that is optionally substituted with a reactive group, or an aryl optionally substituted with C1-C2 alkyl, C1-C2 alkoxy, —Cl, or —F.

Generally, R'$_3$, R'$_4$, R$_a$, R$_b$, R$_c$, and R$_d$ are independently —H, —F, —Cl, —Br, —I, —NO$_2$, —CN, —CO$_2$H, —SO$_3$H, —NHNH$_2$, —SH, —OH, —NH$_2$, substituted or unsubstituted alkoxylcarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl. Alternatively, $R_c$ and $R_d$ in combination and/or $R'_3$ and $R'_4$ in combination can form a saturated or unsaturated 5- or 6-membered ring. Typically, the alkyl and alkoxy portions are C1 to C12. The alkyl or aryl portions of any of the substituents are optionally substituted by —F, —Cl, —Br, —I, alkylamino, cnalkylamino, trialkylammonium (except on aryl portions), alkoxy, alkylthio, aryl, or a reactive group. Generally, $R'_3$, $R'_4$, $R_a$, $R_b$, $R_c$ and $R_d$ are independently —H or unsubstituted alkyl groups. Typically, $R_a$ and $R_c$ are —H and $R'_4$, $R'_3$, $R_b$, and $R_d$ are —H or methyl.

Preferably, the L and L' ligands are the same. Herein, references to L and L' may be used interchangeably.

In Formula 1, c is an integer indicating the charge of the complex. Generally, c is an integer selected from —+1 to +5 indicating a positive charge. For a number of osmium complexes, c is +1, +2, or +3.

X represents counter ion(s). Examples of suitable counter ions include anions, such as halide (e.g., fluoride, chloride, bromide or iodide), sulfate, phosphate, hexafluorophosphate, and tetrafluoroborate, and cations (preferably, monovalent cations), such as lithium, sodium, potassium, tetralkylammonium, and ammonium. Preferably, X is a halide, such as chloride. The counter ions represented by X are not necessarily all the same.

Generally, d represents the number of counter ions and is typically from 1 to 5.

$L_1$ and $L_2$ are ligands attached to the transition metal via a coordinative bond. $L_1$ and $L_2$ are monodentate ligands, at least one of which is a negatively charged monodentate ligand. While $L_1$ and $L_2$ may be used interchangeably, $L_2$ is generally referred to as a negatively charged ligand merely by way of convenience. Herein, the term "negatively charged ligand" is defined as a ligand in which the coordinating atom itself is negatively charged so that on coordination to a positively charged metal, the negative charge is neutralized. For example, a halide such as chloride or fluoride meets the present definition while a pyridine ligand bearing a negatively charged sulfonate group does not because the sulfonate group does not participate in coordination. Examples of negatively charged ligands include, but are not limited to, —F, —Cl, —Br, —I, —CN, —SCN, —OH, alkoxy, alkylthio, and phenoxide. Typically, the negatively charged monodentate ligand is a halide.

Examples of other suitable monodentate ligands include, but are not limited to, $H_2O$, $NH_3$, alkylamine, dialkylamine, trialkylamine, or heterocyclic compounds. The alkyl or aryl portions of any of the ligands are optionally substituted by —F, —Cl, —Br, —I, alkylamino, dialkylamino, trialkylammonium (except on aryl portions), alkoxy, alkylthio, aryl, or a reactive group. Any alkyl portions of the monodentate ligands generally contain 1 to 12 carbons. More typically, the alkyl portions contain 1 to 6 carbons. In other embodiments, the monodentate ligands are heterocyclic compounds containing at least one nitrogen, oxygen, or sulfur atom. Examples of suitable heterocyclic monodentate ligands include imidazole, pyrazole, oxazole, thiazole, triazole, pyridine, pyrazine and derivatives thereof. Suitable heterocyclic monodentate ligands include substituted and unsubstituted imidazole and substituted and unsubstituted pyridine having the general Formulas 3 and 4, respectively, as set forth below.

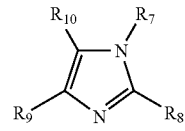

Formula 3

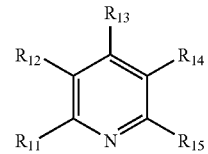

Formula 4

With regard to Formula 3, $R_7$ is generally a substituted or unsubstituted alkyl, alkenyl, or aryl group. Generally, $R_7$ is a substituted or unsubstituted C1 to C12 alkyl or alkenyl, or an aryl, such as phenyl, optionally substituted with a substituent selected from a group consisting of —Cl, —F, —CN, amino, carboxy, C1-C6 alkyl, C1-C6 alkylthio, C1-C6 alkylamino, C1-C6 dialkylamino, C1-C6 alkylaminocarbonyl, C1-C6 alkoxy, C1-C6 alkoxycarbonyl, and C1-C6 alkylcarboxamido. $R_7$ is typically methyl or a C1-C12 alkyl that is optionally substituted with a reactive group, or an aryl optionally substituted with C1-C2 alkyl, C1-C2 alkoxy, —Cl, or —F.

Generally, $R_8$, $R_9$ and $R_{10}$ are independently —H, —F, —Cl, —Br, —I, —NO_2, —CN, —CO_2H, —SO_3H, —NHNH_2, —SH, —OH, —NH_2, alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl. Alternatively, $R_9$ and $R_{10}$, in combination, form a fused 5- or 6-membered ring that is saturated or unsaturated. The alkyl portions of the substituents generally contain 1 to 12 carbons and typically contain 1 to 6 carbon atoms. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. In some embodiments, $R_8$, $R_9$ and $R_{10}$ are —H or substituted or unsubstituted alkyl. Preferably, $R_8$, $R_9$ and $R_{10}$ are —H.

With regard to Formula 4, $R_{11}$, $R_{12}$, $R_{13}$, $R_{14}$ and $R_{15}$ are independently —H, —F, —Cl, —Br, —I, —NO_2, —CN, —CO_2H, —OH, —NH_2, alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl. The alkyl or aryl portions of any of the substituents are optionally substituted by —F, —Cl, —Br, —I, alkylamino, dialkylamino, trialkylammonium (except for aryl portions), alkoxy, alkylthio, aryl, or a reactive group. Generally, $R_{11}$, $R_{12}$, $R_{13}$, $R_{14}$ and $R_{15}$ are —H, methyl, C1-C2 alkoxy, C1-C2 alkylamino, C2-C4 dialkylamino, or a C1-C6 lower alkyl substituted with a reactive group.

One example includes $R_{11}$ and $R_{15}$ as —H, $R_{12}$ and $R_{14}$ as the same and —H or methyl, and $R_{13}$ as —H, C1 to C12 alkoxy, —NH_2, C1 to C12 alkylamino, C2 to C24 dialkylamino, hydrazino, C1 to C12 alkylhydrazino, hydroxylamino, C1 to C12 alkoxyamino, C1 to C12 alkylthio, or C1 to C12 alkyl. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group.

Examples of suitable transition metal complexes include bis[2-(1-methylimidazol-2-yl-κN³)pyridine-κN]chloro(1- methylimidazolo-κN³)osmium(2+) dichloride (also written as [Os(Py-MIM)₂(MIM)Cl]²⁺2Cl⁻) where $L_1$ is

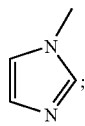

$L_2$ is Cl; c is +2; d is 2; X is Cl−; and L and L' are

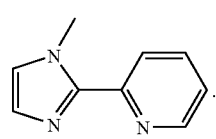

The transition metal complexes of Formula 1 may also include transition metal complexes that are coupled to a polymeric backbone through one or more of L, L', $L_1$, and $L_2$. In some embodiments, the polymeric backbone has at least one functional group that acts as a ligand of the transition metal complex. Such polymeric backbones include, for example, poly(4-vinylpyridine) and poly(N-vinylimidazole) in which the pyridine and imidazole groups, respectively, can act as monodentate ligands of the transition metal complex. In other embodiments, the transition metal complex can be the reaction product between a reactive group on a precursor polymer and a reactive group on a ligand of a precursor transition metal complex (such as complex of Formula 1 where one of L, L', $L_1$, and $L_2$ includes a reactive group, as described above). Suitable precursor polymers include, for example, poly(acrylic acid) (Formula 7), styrene/maleic anhydride copolymer (Formula 8), methylvinylether/maleic anhydride copolymer (GANTREZ polymer) (Formula 9), poly(vinylbenzylchloride) (Formula 10), poly(allylamine) (Formula 11), polylysine (Formula 12), carboxy-poly(vinylpyridine) (Formula 13), and poly(sodium 4-styrene sulfonate) (Formula 14). The numbers n, n' and n" appearing variously in these formulas may vary widely. Merely by way of example, in Formula 13, [n'/(n'+n")]×100% is preferably from about 5% to about 15%.

Formula 7
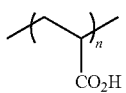

Formula 8
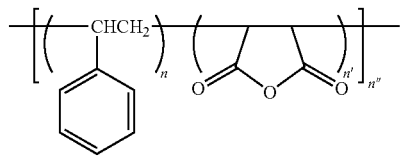

Formula 9
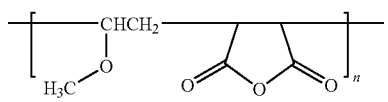

Formula 10
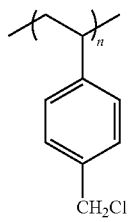

Formula 11

Formula 12
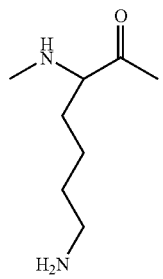

Formula 13
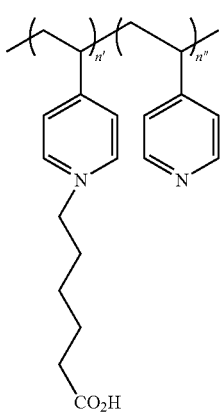

Formula 14
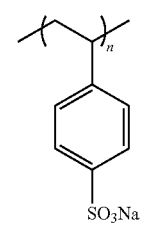

Alternatively, the transition metal complex can have one or more reactive group(s) for immobilization or conjugation of the complexes to other substrates or carriers, examples of which include, but are not limited to, macromolecules (e.g., enzymes) and surfaces (e.g., electrode surfaces).

For reactive attachment to polymers, substrates, or other carriers, the transition metal complex precursor includes at least one reactive group that reacts with a reactive group on the polymer, substrate, or carrier. Typically, covalent bonds are formed between the two reactive groups to generate a linkage. Examples of such reactive groups and resulting linkages are provided in Table 1, below. Generally, one of the reactive groups is an electrophile and the other reactive group is a nucleophile.

TABLE 1

Examples of Reactive Groups and Resulting Linkages

| First Reactive Group | Second Reactive Group | Resulting Linkage |
|---|---|---|
| Activated ester* | Amine | Carboxamide |
| Acrylamide | Thiol | Thioether |
| Acyl azide | Amine | Carboxamide |
| Acyl halide | Amine | Carboxamide |
| Carboxylic acid | Amine | Carboxamide |
| Aldehyde or ketone | Hydrazine | Hydrazone |
| Aldehyde or ketone | Hydroxyamine | Oxime |
| Alkyl halide | Amine | Alkylamine |
| Alkyl halide | Carboxylic acid | Carboxylic ester |
| Alkyl halide | Imidazole | Imidazolium |
| Alkyl halide | Pyridine | Pyridinium |
| Alkyl halide | Alcohol/phenol | Ether |
| Alkyl halide | Thiol | Thioether |
| Alkyl sulfonate | Thiol | Thioether |
| Alkyl sulfonate | Pyridine | Pyridinium |
| Alkyl sulfonate | Imidazole | Imidazolium |
| Alkyl sulfonate | Alcohol/phenol | Ether |
| Anhydride | Alcohol/phenol | Ester |
| Anhydride | Amine | Carboxamide |
| Aziridine | Thiol | Thioether |
| Aziridine | Amine | Alkylamine |
| Aziridine | Pyridine | Pyridinium |
| Epoxide | Thiol | Thioether |
| Epoxide | Amine | Alkylamine |
| Epoxide | Pyridine | Pyridinium |
| Halotriazine | Amine | Aminotriazine |
| Halotriazine | Alcohol | Triazinyl ether |
| Imido ester | Amine | Amidine |
| Isocyanate | Amine | Urea |
| Isocyanate | Alcohol | Urethane |
| Isothiocyanate | Amine | Thiourea |
| Maleimide | Thiol | Thioether |
| Sulfonyl halide | Amine | Sulfonamide |

*Activated esters, as understood in the art, generally include esters of succinimidyl, benzotriazolyl, or aryl substituted by electron-withdrawing groups such as sulfo, nitro, cyano, or halo; or carboxylic acids activated by carbodiimides.

Transition metal complexes of the present invention can be soluble in water or other aqueous solutions, or in organic solvents. In general, the transition metal complexes can be made soluble in either aqueous or organic solvents by having an appropriate counter ion or ions, X. For example, transition metal complexes with small counter anions, such as $F^-$, $Cl^-$, and $BC$, tend to be water soluble. On the other hand, transition metal complexes with bulky counter anions, such as $I^-$, $BF_4^-$ and $PF_6^-$, tend to be soluble in organic solvents. Preferably, the solubility of transition metal complexes of the present invention is greater than about 0.1 M (moles/liter) at 25° C. for a desired solvent.

The transition metal complexes discussed above are useful as redox mediators in electrochemical sensors for the detection of analytes in biofluids. The use of transition metal complexes as redox mediators is described, for example, in U.S. Pat. Nos. 5,262,035, 5,320,725, 5,365,786, 5,593,852, 5,665, 222, 5,972,199, 6,134,161, 6,143,164, 6,175,752 and 6,338, 790 and U.S. patent application Ser. No. 09/434,026, all of which are incorporated herein by reference. The transition metal complexes described herein can typically be used in place of those discussed in the references listed above, although the results of such use will be significantly enhanced given the particular properties of the transition metal complexes of the present invention, as further described herein.

In general, the redox mediators of the present invention are disposed on or in proximity to (e.g., in a solution surrounding) a working electrode. The redox mediator transfers electrons between an analyte and a working electrode. In some preferred embodiments, an enzyme is also included to facilitate the transfer. For example, the redox mediator transfers electrons between glucose and the working electrode (typically via an enzyme) in an enzyme-catalyzed reaction of glucose. Redox polymers are also be particularly useful for forming non-leachable coatings on the working electrode. These can be formed, for example, by crosslinking the redox polymer on the working electrode, or by crosslinking the redox polymer and the enzyme on the working electrode.

Transition metal complexes can enable accurate, reproducible and quick or continuous assays. Transition metal complex redox mediators accept electrons from, or transfer electrons to, enzymes or analytes at a high rate and also exchange electrons rapidly with an electrode. Typically, the rate of self exchange, the process in which a reduced redox mediator transfers an electron to an oxidized redox mediator, is rapid. At a defined redox mediator concentration, this provides for more rapid transport of electrons between the enzyme (or analyte) and electrode, and thereby shortens the response time of the sensor. Additionally, the novel transition metal complex redox mediators are typically stable under ambient light and at the temperatures encountered in use, storage and transportation. Preferably, the transition metal complex redox mediators do not undergo chemical change, other than oxidation and reduction, in the period of use or under the conditions of storage, though the redox mediators can be designed to be activated by reacting, for example, with water or the analyte.

The transition metal complexes can be used as redox mediators in combination with redox enzymes to electrooxidize or electroreduce the analyte or a compound derived of the analyte, for example by hydrolysis of the analyte. The redox potentials of the redox mediators are generally more positive (i.e. more oxidizing) than the redox potentials of the redox enzymes when the analyte is electrooxidized and more negative when the analyte is electroreduced. For example, the redox potentials of the preferred transition metal complex redox mediators used for electrooxidizing glucose with glucose oxidase, FAD-glucose dehydrogenase or PQQ-glucose dehydrogenase as the enzyme is between about −200 mV and +200 mV versus a Ag/AgCl reference electrode, and the most preferred mediators have redox potentials between about −200 mV and about +100 mV versus a Ag/AgCl reference electrode.

Examples of Syntheses of Transition Metal Complexes

Examples showing the syntheses of various transition metal complexes that are useful as redox mediators are provided below. Unless indicated otherwise, all of the chemical reagents are available from Aldrich Chemical Co. (Milwaukee, Wis.) or other sources. Numerical figures provided are approximate.

EXAMPLE 1

Synthesis of $[Os(Py-MIM)_2(X)Cl]^{2+}2Cl^-$ Complexes

By way of illustration, examples of the syntheses of [Os (Py-MIM)$_2$(MAP)Cl]$^{2+}$2Cl$^-$ ("MAP") and [Os(Py-MIM)$_2$ (MIM)Cl]$^{2+}$2Cl$^-$ ("MIM") as illustrated below, are now provided. As described herein, [Os(Py-MIM)$_2$(MAP)Cl]$^{2+}$2Cl$^-$ is a transition metal complex that is particularly useful as a redox mediator.

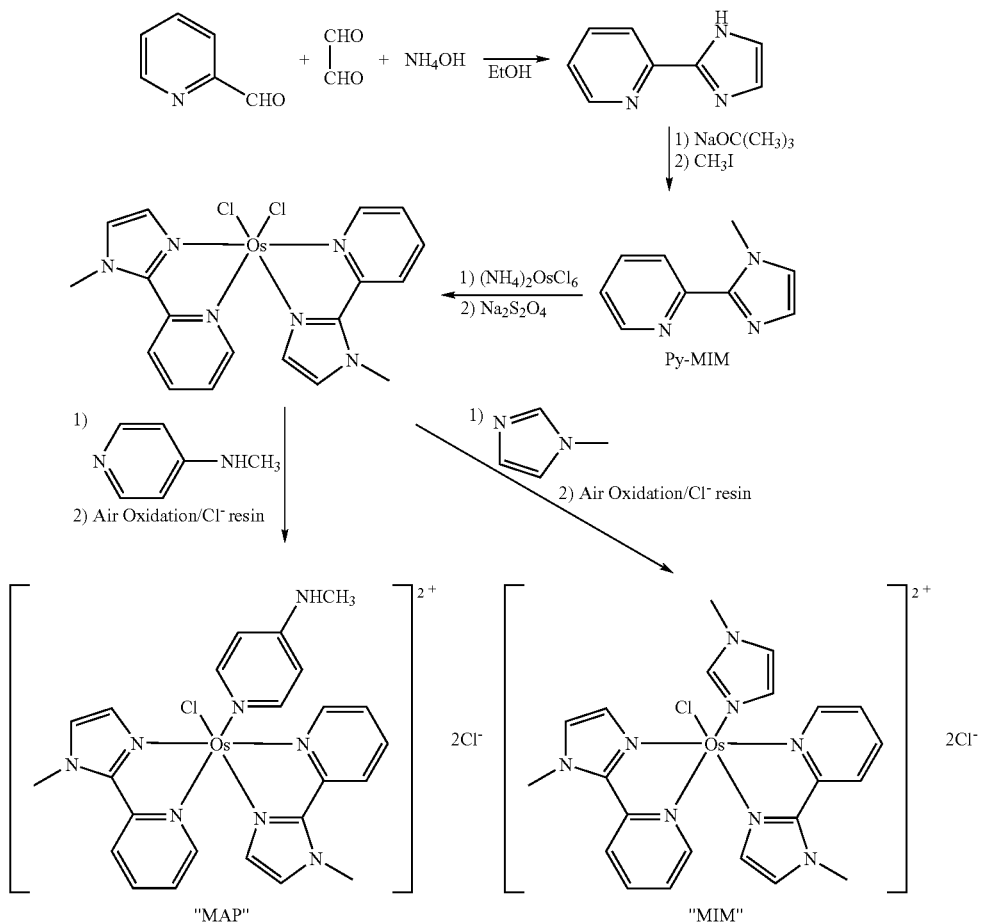

Synthesis of 2-(1H-imidazol-2-yl)pyridine (=pyridyl-imidazole)

A solution of pyridine-2-carboxaldehyde (151.4 g, 1.41 mol) and glyoxal (40% in $H_2O$, 205 mL, 1.79 mol) in 300 mL of ethanol (EtOH) in a three-neck 1 L round-bottom flask fitted with a thermometer and an addition funnel was stirred in an ice bath. When the solution was cooled to below 5° C., concentrated $NH_4OH$ (28-30%, 482 mL, 3.93 mol) was added dropwise through the addition funnel. The rate of the addition was controlled so that the temperature of the solution was maintained at below 5° C. After the addition, the stirring of the solution was continued in the ice bath for one hour and then at room temperature overnight. During the stirring process, the solution changed from light yellow to dark brown.

The solution was transferred to a 2 L round bottom flask and the EtOH solvent was removed by rotary evaporation. The resulting dark viscous material was transferred to a 4 L beaker with 700 mL of EtOAc. Saturated NaCl (500 mL) was added and the mixture was stirred for 2 hours. The solution was poured into a 2 L separation funnel and a dark tarry material was discarded. The organic layer was separated from the solution and the aqueous layer was extracted several times with EtOAc (500 mL EtOAc per extraction). The organic layer was then dried with anhydrous $Na_2SO_4$ overnight, whereupon the resulting mixture was gravity filtered, the $Na_2SO_4$ was washed with EtOAc (4×50 mL), and the solution was concentrated to about 300-400 mL by rotary evaporation. The concentrated solution was transferred to a 1 L Erlenmeyer flask and the volume was adjusted with more EtOAc to about 400-500 mL, as necessary. The solution stood at 4° C. for 1-2 days to form large amber crystals. The crystals were collected by suction filtration and washed with cold EtOAc (20-30 mL). The filtrate contained a large amount of product, so further concentration and crystallization procedures were performed. The crystals were combined and dried at 40-45° C. under high vacuum for 2 days. The yield of 2-(1H-imidazol-2-yl)pyridine was about 75 g (33%).

Synthesis of 2-(1-methyl-1H-imidazol-2-yl)pyridine (=Py-MIM)

Pyridine-2-carboxaldehyde (50.5 g, 0.47 mol) and glyoxal (40% in $H_2O$, 68.3 mL, 0.60 mol) in 100-150 mL of ethanol (EtOH) in a three-neck 1 L round-bottom flask fitted with a thermometer and an addition funnel were stirred in an ice bath. When the solution was cooled to below 5° C., concentrated $NH_4OH$ (28-30%, 161 mL, 1.31 mol) was added dropwise through the addition funnel. The rate of the addition was controlled so that the temperature of the solution was maintained at below 5° C. After the addition, the stirring of the solution was continued in the ice bath for one hour and then at room temperature overnight. During the stirring process, the solution changed from light yellow to dark brown.

The solution was transferred to a 1 L round bottom flask and the EtOH and $H_2O$ solvents were removed by rotary evaporation at 50° C. The resulting material was dried further at about 50° C. under high vacuum for 24 hours and then dissolved in anhydrous dimethylformamide (DMF), whereupon the solution was transferred with further DMF (total DMF 450-500 mL) to a three-neck 1 L round bottom flask equipped with a reflux condenser, and then stirred. Sodium t-butoxide (48.9 g, 0.51 mol) was added quickly via funnel to obtain, with continued stirring for about 1 hour, a dark brown homogeneous solution. Methyl iodide (34.5 mL, 0.56 mol) was then added dropwise via addition funnel over 1.5-2 hours, resulting in a white precipitate of NaI. The mixture was stirred at room temperature overnight, its color changing from dark brown to light brown. The mixture was then poured into a beaker containing 1.5 mL of EtOAc and suction-filtered using a Buchner funnel to remove the NaI precipitate. The precipitate was washed with additional EtOAc (3×100 mL). The filtrate was transferred to a 2 L round bottom flask and concentrated by rotary evaporation to remove the EtOAc.

The resulting viscous material was transferred to a 1 L beaker with a minimum amount of EtOAc, which was then removed by rotary evaporation. The remaining DMF was removed by vacuum distillation using a low vacuum diaphragm pump and an oil bath. Upon complete removal of the DMF, the product was distilled at 100-110° C. under high vacuum. The yield of 2-(1-methyl-1H-imidazol-2-yl)pyridine was about 36 g (48%).

Synthesis of Os(Py-MIM)$_2$Cl$_2$ 2-(1-methyl-1H-imidazol-2-yl)pyridine (3.4 g, 21.4 mmol) and ammonium hexachloroosmiate (IV) (4.7 g, 10.7 mmol) were combined with anhydrous ethylene glycol (86 mL) in a three-neck 250 mL round-bottom flask, fitted with a reflux condenser, immersed in a temperature-controlled oil bath. The reaction mixture was degassed with N$_2$ for about 15 minutes. The mixture was stirred under N$_2$ while the heater was turned on to heat the oil bath, and the reaction proceeded at 130° C. for 2 hours and subsequently at 140° C. for about 28 hours until an intermediate that was formed in the reaction was completely converted to the final product. The solution was cooled to room temperature and then suction-filtered through a fritted funnel into a three-neck 250 mL round bottom flask, whereupon a small amount of orange precipitate left in the funnel was discarded. The solution (solution A) was then degassed with N$_2$ for 15 minutes and kept under N$_2$.

Deionized H$_2$O (320 mL) was then degassed with N$_2$ in a three-neck 500 mL round bottom flask cooled in an ice/water bath and equipped with a thermometer. After 15 minutes of degassing, sodium hydrosulfite (85%, 9.31 g, 53.5 mmol) under N$_2$ was added immediately and degassing continued for another 10-15 minutes. The temperature of the solution (solution B) was below 5° C. Solution A was then added via canula to solution B under rapid stirring for about 0.5 hour to form a fine dark purple precipitate of Os(Py-MIM)$_2$Cl$_2$. Stirring continued under N$_2$ for another 0.5 hour. The resulting suspension was suction-filtered through a 0.4 or 0.3 micron Nylon membrane. The suspension was transferred to the suction funnel via canula under nitrogen to minimize air exposure. The dark purple precipitate was then washed with a minimum of ice cold water (2×5 mL). The precipitate was immediately dried by lyophilization for at least 24 hours. The yield of Os(Py-MIM)$_2$Cl$_2$ was about 5.6 g (crude).

Synthesis of [Os(Py-MIM)$_2$(MAP)Cl]$^{2+}$2Cl$^-$

To Os(Py-MIM)$_2$Cl$_2$ (10 g, 17.3 mmol), in a 2-L three-neck round bottom flask fitted with a reflux condenser, was added, under a positive pressure of Ar, anhydrous ethanol (0.9 L), 4-(methylamino)pyridine (3.72 g, 34.4 mmol), and activated 4 Å molecular sieves (30 g). The mixture was heated to reflux and stirred magnetically for 17 h and then filtered hot through Whatman #1 on a Büchner funnel. The filtrate was concentrated by rotary evaporation down to about 20 mL, then diluted with anh. EtOH to 25 mL. This solution was then added via syringe pump over 1 h to vigorously stirring MTBE (0.7 L). The mixture was stirred a further 1 h after the addition was complete, and then filtered on a Büchner funnel. The collected ppt was suctioned dry for 15 min, and then transferred to a beaker, redissolving in a total of 500 mL deionized water. Chloride resin (BioRad AG1-X4, c. 40 mL, prerinsed with 200 mL deionized water), was added and the mixture stirred overnight in air to oxidize the product. The mixture was again filtered and the filtrate lyophilized to yield 10.3 g crude [Os(Py-MIM)$_2$(MAP)Cl]$^{2+}$2Cl$^-$.

The crude material was then purified by LH-20 chromatography as follows: A solution of 1 g crude [Os(Py-MIM)$_2$(MAP)Cl]$^{2+}$2Cl$^-$ in 6.5 mL column solvent was loaded onto an 800 mL (5×40 cm) LH-20 column packed in [EtOH: 0.1M NH$_4$OH (1:1)] and eluted at 2.5 mL/min. Product elutes as a dark red band (0.64 g after lyophilization, 35% overall yield from the hexachloroosmiate).

As described herein, [Os(Py-MIM)$_2$(MAP)Cl]$^{2+}$2Cl$^-$ is a transition metal complex that is particularly useful as a redox mediator.

Synthesis of [Os(Py-MIM)$_2$(MIM)Cl]$^{2+}$2Cl$^-$

Anhydrous ethanol (1 L) in a 2-L three-neck round bottom flask fitted with a reflux condenser was degassed with N$_2$ for 15 minutes. Os(Py-MIM)$_2$Cl$_2$ (3.1 g, 5.35 mmol) was added quickly under N$_2$ via a funnel. The suspension was stirred and heated to reflux. 1-Methyl-1H-imidazole (0.43 mL, 5.35 mmol) was then added at once via syringe. Reflux continued until the reaction was completed. During the reaction, the solution changed from dark brown to purple-brown. The solution was cooled to room temperature and then suction-filtered through a fritted funnel. The solvent was then removed by rotary evaporation to give the crude product in its reduced form.

The product was transferred with 30-50 mL H$_2$O to a 400 mL beaker containing about 40 mL AG1-X4 chloride resin from Bio-Rad, or preferably, 80 mL Dowex-1-chloride from Aldrich. The mixture was stirred in open air for about 24 hours to convert Os(II) to Os(III). The mixture was then suction-filtered and the resin was washed with H$_2$O (5×30 mL). The combined filtrate was concentrated to about 50 mL by rotary evaporation at 35° C. under vacuum.

The solution was loaded onto a LH-20 column (2"×22"), which was eluted with H$_2$O. 50 mL fractions were collected and analyzed by CV to find the major purple-brown band associated with the product. Fractions containing pure product were collected and concentrated by rotary evaporation to about 150 mL. The solution was then freeze-dried to give the product. The yield of [Os(Py-MIM)$_2$(MIM)Cl]$^{2+}$2Cl$^-$ was about 2.4 g (58% from the hexachloroosmiate).

As described herein, [Os(Py-MIM)$_2$(MIM)Cl]$^{2+}$2Cl$^-$ is a transition metal complex that is particularly useful as a redox mediator.

EXAMPLE 2

Synthesis of [Os(pMOP-IM)$_2$(biMIM)]$^{3+}$3Cl$^-$

By way of further illustration, an example of the synthesis of [Os(pMOP-IM)$_2$(biMIM)]$^{3+}$3Cl$^-$ ("Dimethoxy"), as illustrated below, is now provided. This example demonstrates how a substitution can be introduced into the Py-MIM ligand as a means of generating mediators that work with FAD-GDH.

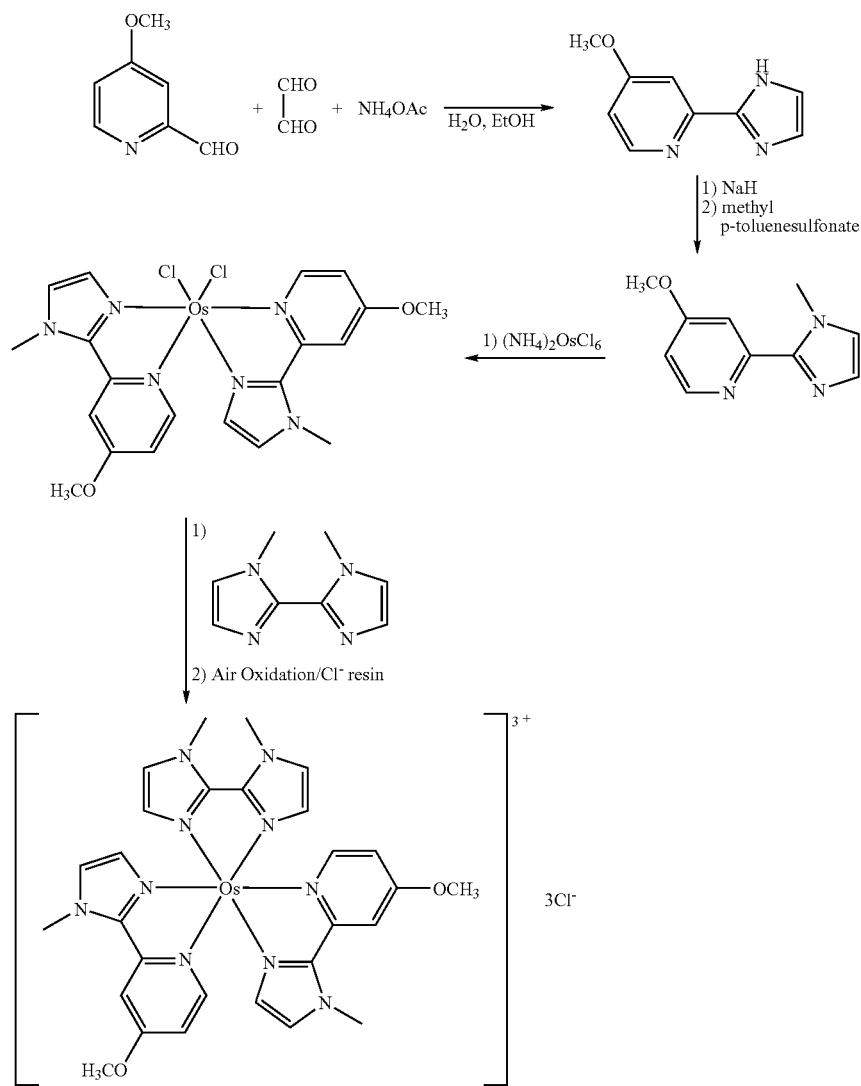

Synthesis of 4-methoxy-2-(1H-imidazol-2-yl)pyridine

To a suspension of ammonium acetate (1.13 g, 14.6 mmol) in 0.2 mL water at 45° C. with mechanical stirring in air, was added a suspension of 4-methoxypyridine carboxaldehyde (Milestone, 0.50 g, 3.65 mmol), glyoxal (40%, 0.50 mL, 4.38 mmol), and 0.87 mL ethanol portionwise over 2.5 h. Rinsed with 0.15 mL ethanol to complete the addition, and stirred a further 30 min at 45° C., then at room temperature overnight. Added 8 mL water, then filtered through Celite. To the filtrate was added dropwise with stirring, 1.4 mL 10% NaOH, then 0.43 g $Na_2CO_3$. Extracted with chloroform (3×10 mL), and washed the combined organic layers with 5 mL brine. Dried over $Na_2SO_4$, and concentrated by rotary evaporation followed by high vacuum overnight, to yield 0.42 g crude 4-methoxy-2-(1H-imidazol-2-yl)pyridine as a brown oil.

Synthesis of 4-methoxy-2-(1-methyl-1H-imidazol-2-yl)pyridine (pMOP-MIM)

To crude 4-methoxy-2-(1H-imidazol-2-yl)pyridine (0.40 g, 2.28 mmol) in 7.5 mL anhydrous DMF with magnetic stirring under Ar at 0° C., NaH (60% in oil, 91 mg, 2.28 mmol) was added portionwise. Stirred at 0-5° C. for 1 h, then added a solution of methyl-p-toluenesulfonate (0.344 mL, 2.28 mmol) in 0.75 mL anh. DMF dropwise with stirring. After 15 min, the ice bath was removed and the reaction mixture stirred for 2 h at room temp. Cooled back to 0° C. and quenched by very carefully adding 10% aq. $Na_2CO_3$ dropwise (about 10 mL total). Extracted 2×30 mL chloroform. Combined organic layers were washed with brine (5 mL), dried over $Na_2SO_4$ and concentrated to give 0.73 g as a dual-phase oil. Chromatographed on 18 g silica gel in 0-2% $MeOH/CHCl_3$+0.5% TEA to yield 0.20 g (45%) of 4-methoxy-2-(1-methyl-1H-imidazol-2-yl)pyridine.

Synthesis of $[Os(pMOP-MIM)_2(biMIM)]^{3+}3Cl^-$

In a 25-mL one-neck pear flask, 4-methoxy-2-(1-methyl-1H-imidazol-2-yl)pyridine (75 mg, 0.40 mmol), was dried by azeotrope with toluene, then dissolved in anhydrous ethylene glycol under Ar, and added ammonium hexachloroosmiate (IV) (87 mg, 0.20 mmol), degassing by iteratively evacuating and backfilling with Ar. Under a positive pressure of Ar, the reaction mixture was heated to 130° C. for 2 h, then at 140° C. for 28 h. The reaction was cooled to room temp, still under positive Ar pressure, and 1,1'-dimethyl bi-1H-imidazole (prepared via literature methods, 32 mg, 0.20 mmol), was added as a solid. Heated again to 140° C. for 26 h, and cooled to room temp.

The crude reaction mixture was diluted with 57 mL water and loaded atop a 25-mL presoaked column of HP-20 resin. Loaded over 2 h, and eluted with water. Combined first few fractions (product) and stirred overnight in open air. Filtered via Büchner and added the appr. 45 mL without further dilution, dropwise over 3 h to a stirring solution of $NH_4PF_6$ (7.5 g in 27 mL $H_2O$). After stirring for 5 days, the ppt was filtered off using Whatman #1 on a Büchner funnel. The brown ppt was suctioned dry for 10 min, then redissolved in 5 mL $CH_3CN$, filtering out the residual clear salt. The filtrate was transferred to a 100 mL beaker, c. 5 mL of prewashed AG1-X4 chloride resin (BioRad) was added, and stirred for 15 min. Deionized water (20 mL) was added over 30 min, and the mixture was stirred overnight. Filtered and lyophilized to yield 51 mg (30%) of $[Os(pMOP-MIM)_2(biMIM)]^{3+}3Cl^-$ as a dark brown solid.

EXAMPLE 3

Synthesis of 2-(1-phenyl-1H-imidazol-2-yl)pyridine (Py-PIM)

By way of further illustration, an example of the synthesis of 2-(1-phenyl-1H-imidazol-2-yl)pyridine, as illustrated below, is now provided. This example demonstrates how a 1-aryl-substituted 2-(2-pyridyl)imidazole is made from 1-(2-pyridyl)imidazole or its derivative, and an iodobenzene derivative (as illustrated) or a bromobenzene derivative.

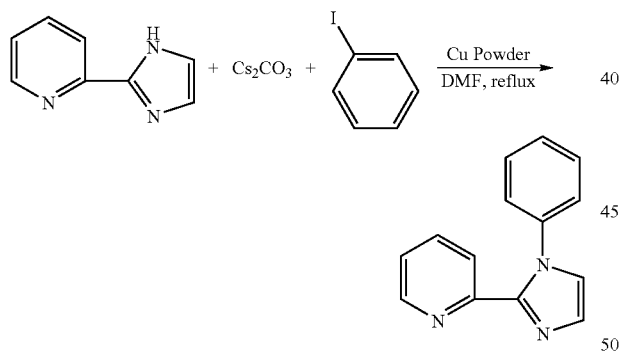

2-(1H-imidazol-2-yl)pyridine (6.91 g), iodobenzene (11.47 g), $Cs_2CO_3$ (25 g), and copper powder (15 g) were combined in 60 mL anhydrous DMF in a 250 mL round bottom flask equipped with a magnetic stirrer and a reflux condenser. The mixture was degassed with $N_2$ for 15 minutes at room temperature and then refluxed under $N_2$ in an oil bath for 24 hours. The resulting mixture was cooled to room temperature and suction-filtered to remove the solid byproduct. The filtrate was extracted with EtOAc (3×100 mL). The combined organic layers were washed with $H_2O$ (2×100 mL), then with saturated NaCl (2×150 mL), and subsequently dried with anhydrous $Na_2SO_4$. Evaporation of the solvent gave crude 2-(1-phenyl-1H-imidazol-2-yl)pyridine. The crude product is generally pure enough to use in making redox mediators, although the crude product may be further purified using a silica gel column and eluting with $MeOH/CHCl_3$.

The 2-(1-phenyl-1H-imidazol-2-yl)pyridine product described above can be used to synthesize transition metal complexes in much the same manner 2-(1-methyl-1H-imidazol-2-yl)pyridine was used in Example 1 above.

EXAMPLE 4

Comparison of Glucose Oxidation Currents from Different Mediators in PBS

Mediators were first dissolved in PBS at a concentration of 3.0 mg/ml. The solution was subsequently spiked with 1M glucose so that each contained 10 mM glucose. The mediator- and glucose-containing solutions were then fed into FREESTYLE® strips containing FAD-GDH, but no mediators in the strip chemistry. A potential of +100 mV was applied across the carbon and silver electrodes and the resulting current was recorded. The magnitude of the peak currents indicate the rate of the electrocatalytic oxidation of glucose facilitated by different mediators. Two measurements were performed on each solution. Peak currents are tabulated below. Each mediator shows a higher peak current than nPBI.

|  | Peak Currents | | |
| --- | --- | --- | --- |
| Mediator Name | Ip-1 | Ip-2 | Average Ip |
| $Os(bi-pMOP)_2(MIM)Cl_3$ ("DMO") | 52.3 | 56.5 | 54.4 |
| $Os(Py-MIM)_2(nPBI)Cl_3$ ("nPBI") | 16.3 | 22.8 | 19.6 |
| $Os(Py-MIM)_2(MAP)Cl_3$ ("MAP") | 38.7 | 40.8 | 39.8 |
| $Os(Py-MIM)_2(DMAP)Cl_3$ ("DMAP") | 34.2 | 31.5 | 32.9 |
| $Os(Py-MIM)_2(4-HP)Cl_3$ ("4-HP") | 28.9 | 29.8 | 29.4 |
| $Os(Py-MIM)_2(pMOP)Cl_3$ ("p-MOP") | 37.1 | 32.9 | 35.0 |
| $Os(Py-MIM)_2(mMOP)Cl_3$ ("m-MOP") | 34.2 | 35.4 | 34.8 |
| $Os(pMOP-MIM)_2(biMIM)_2Cl_3$ ("Dimethoxy") | 28.3 | 28.4 | 28.4 |
| $Os(MPI)_2(AP)Cl_3$ ("NH_2") | — | — | — |

EXAMPLE 5

Comparison of FAD-GDH FREESTYLE® Strip Performance from Different Mediators in Blood DMO, p-MOP, and MAP were coated with FAD-GDH in FREESTYLE® strips. The strips were tested with 200 mg/dL blood with 8 replicates. A potential of 0 mV was applied to the FREESTYLE® meter. The results are summarized in the following table:

| | | FAD-026 0 mV | | |
| --- | --- | --- | --- | --- |
| Strip | No. | Glucose reference[1] | Avg (Peak Cur) | Avg (Resp time) |
| DMO | 8 | 199 | 29.3 | 13.1 sec |
| p-MOP | 8 | 199 | 22.6 | 14.7 sec |
| MAP | 8 | 199 | 33.6 | 12.1 sec |

[1]YSI Life Sciences (Yellow Springs, Ohio)

EXAMPLE 6

Comparison of FAD-GDH FREESTYLE® Strip Performance from Different Mediators in Blood DMO, p-MOP, and MAP were coated with FAD-GDH in FREESTYLE® strips. The strips were tested with 200 mg/dL blood with 6-8 replicates. A potential of 100 mV was applied to the FREESTYLE® meter. The results are summarized in the following table:

| Strip | No. | Glucose reference[2] | Avg (Peak Cur) | Avg (Resp time) |
|---|---|---|---|---|
| 1xDMO | 7 | 206 | 31.9 | 7.6 sec |
| 2xDMO | 8 | 206 | 36.2 | 6.8 sec |
| 1xDMAP | 8 | 206 | 30.2 | 9.0 sec |
| 2xDMAP | 8 | 206 | 36.5 | 7.3 sec |
| 1xp-MOP | 8 | 206 | 33.4 | 7.2 sec |
| 2xp-MOP | 8 | 206 | 41.4 | 6.9 sec |

FAD-024 100 mV

[2]YSI Life Sciences (Yellow Springs, Ohio)

The mediators referred to as "MAP" bis[2-(1-methylimidazol-2-yl-κN³)pyridine-κN]chloro[4-(methylamino)pyridine-κN¹)osmium(2+) dichloride and "p-MOP" bis[2-(1-methylimidazol-2-yl-κN³)pyridine-κN]chloro(4-methoxypyridine-κN¹)osmium(2+) dichloride perform well as mediators with FAD-GDH. MAP and p-MOP show higher peak currents than the mediator referred to as "nPBI" (Example 4). They also show comparable response times with the mediator referred to as "DMO" (Example 5). They are also known to perform well with the PQQ-GDH enzyme.

Examples of Transition Metal Complexes

Transition metal complexes that serve as redox mediators according to the present invention are provided in Table 2 below, as Mediator Nos. 1-21. The redox potentials ($E_{1/2}$ (mV) relative to a standard Ag/AgCl reference electrode in a pH 7 PBS buffer) associated with these redox mediators are also provided, where available.

Also provided in Tables 3 and 4 are various of these redox mediators and their associated redox potentials and associated slopes, k, of substantially linear plots of collected charge (μC) versus glucose concentration (mg/dL) for a given volume (~315 ηL) of biofluid, such as blood, as further described below. Comparative information for known redox mediators, namely, Comparative Mediator Nos. I, X, XII and XIII is also provided. The slope data in Table 3 and Table 4 concerns redox mediators tested under Condition A and Condition B, respectively, which reflect different ink lots, as now described.

That is, these slope data were obtained from individual tests in which each mediator and an enzyme mixture were coated on a working electrode. The working electrode was made of a conductive ink layered over a plastic substrate. The working electrode was laminated together with a counter/reference electrode, using standard processing known in the art. The counter/reference electrode was made of a Ag/AgCl ink layered over a plastic substrate. Variations are routinely observed in test strip sensors made from different ink lots. Thus, in Table 3, Condition A refers to tests conducted using a series of test strips made from a single lot, and in Table 4, Condition B similarly refers to tests conducted using a series of test strips made from a single lot, different from that associated with Condition A. Thus, comparisons of slope data shown in Table 3 and Table 4 should not be made, while comparisons of slope data shown within either Table 3 or Table 4 are instructive as to mediator performance.

TABLE 2

Examples of Low Potential Mediators of the Present Invention

| Mediator No. | Structure of Mediator | $E_{1/2}$ (mV) Redox Potential, versus Ag/AgCl |
|---|---|---|
| 1 | 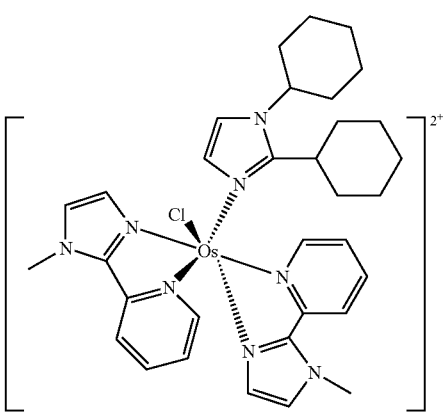 | −164 |

TABLE 2-continued

Examples of Low Potential Mediators of the Present Invention

| Mediator No. | $E_{1/2}$ (mV) Structure of Mediator | Redox Potential, versus Ag/AgCl |
|---|---|---|
| 2 | [structure with Os center, 2Cl⁻, 2+ charge] | −168 |
| 3 | [structure with Os center, 2Cl⁻, 2+ charge] | −150 |
| 4 | [structure with Os center, 2Cl⁻, 2+ charge] | −172 |
| 5 | [structure with Os center, 2Cl⁻, 2+ charge] | |

TABLE 2-continued

Examples of Low Potential Mediators of the Present Invention

| Mediator No. | Structure of Mediator | $E_{1/2}$ (mV) Redox Potential, versus Ag/AgCl |
|---|---|---|
| 6 | [Os complex structure with N-methylimidazole-(4-chlorophenyl), N-methylimidazole-pyridine, N-methylimidazole-pyridine ligands and Cl]$^{2+}$ 2Cl$^-$ | |
| 7 | [Os complex structure with N-methylbenzimidazole-pyridine, N-methylimidazole-pyridine, N-methylimidazole-pyridine ligands and Cl]$^{2+}$ 2Cl$^-$ | −154 |
| 8 | [Os complex structure with (3-fluorophenyl)-phenyl-imidazole, N-methylimidazole-pyridine, N-methylimidazole-pyridine ligands and Cl]$^{2+}$ 2Cl$^-$ | −139 |

TABLE 2-continued

Examples of Low Potential Mediators of the Present Invention

| Mediator No. | Structure of Mediator ($E_{1/2}$ (mV)) | Redox Potential, versus Ag/AgCl |
|---|---|---|
| 9 | [structure] | −124 |
| 10 | [structure] | −117 |
| 11 | [structure] | −130 |
| 12 | [structure] | −166 |

TABLE 2-continued

Examples of Low Potential Mediators of the Present Invention

| Mediator No. | Structure of Mediator | $E_{1/2}$ (mV) Redox Potential, versus Ag/AgCl |
|---|---|---|
| 13 | [structure] | −88 |
| 14 | [structure] Os(MPI)$_2$(m-MOP)Cl$_3$ "m-MOP" bis[2-(1-methylimidazol-2-yl-κN$^3$)pyridine-κN]chloro(3-methoxypyridine-κN$^1$)osmium(2+) dichloride | −30 |
| 15 | [structure] Os(MPI)$_2$(m-MOP)Cl$_3$ "p-MOP" bis[2-(1-methylimidazol-2-yl-κN$^3$)pyridine-κN]chloro(4-methoxypyridine-κN$^1$)osmium(2+) dichloride | −90 |

TABLE 2-continued

Examples of Low Potential Mediators of the Present Invention

| Mediator No. | Structure of Mediator | Redox Potential, $E_{1/2}$ (mV) versus Ag/AgCl |
|---|---|---|
| 16 | Os(MPI)$_2$(DMAP)Cl$_3$ "DMAP" bis[2-(1-methylimidazol-2-yl-κN$^3$)pyridine-κN]chloro(4-(dimethylamino)pyridine-κN$^1$)osmium(2+) dichloride | −155 |
| 17 | Os(MPI)$_2$(MAP)Cl$_3$ "MAP" bis[2-(1-methylimidazol-2-yl-κN$^3$)pyridine-κN]chloro[4-(methylamino)pyridine-κN$^1$]osmium(2+) dichloride | −160 |
| 18 | Os(MPI)$_2$(4HP)Cl$_3$ "4-HP" bis[2-(1-methylimidazol-2-yl-κN$^3$)pyridine-κN]chloro[4-hydroxypyridine-κN$^1$]osmium(2+) dichloride | −185 |

TABLE 2-continued

Examples of Low Potential Mediators of the Present Invention

| Mediator No. | $E_{1/2}$ (mV) Structure of Mediator | Redox Potential, versus Ag/AgCl |
|---|---|---|
| 19 | 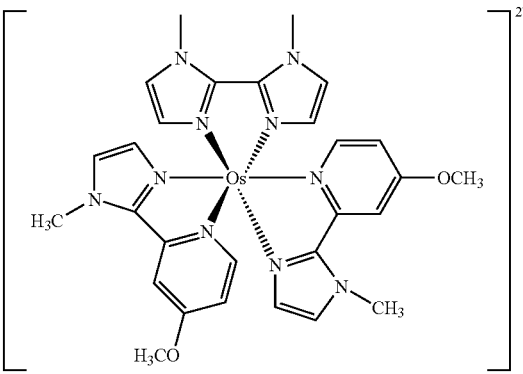<br>Os(MIMOP)$_2$(MI)$_2$Cl$_2$ "Dimethoxy" bis[2-(1-methylimidazol-2-yl-κN$^3$)-4-methoxypyridine-κN](1,1'-dimethyl-2,2'-biimidazole κN$^3$,N$^{3'}$)osmium(2+) dichloride | −78 |
| 20 | 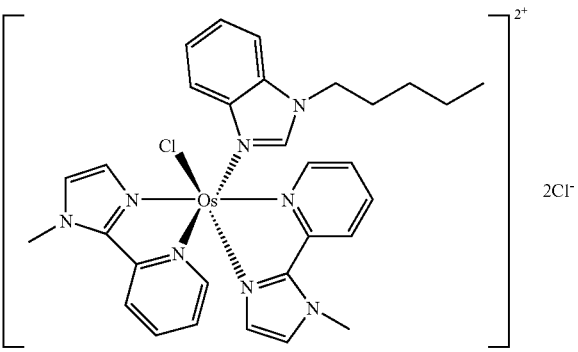<br>"nPBI" bis[2-(1-methylimidazol-2-yl-κN$^3$)pyridine-κN](chloro(1-pentylbenzimidazole-κN$^3$)osmium(2+) dichloride | −125 |
| 21 | 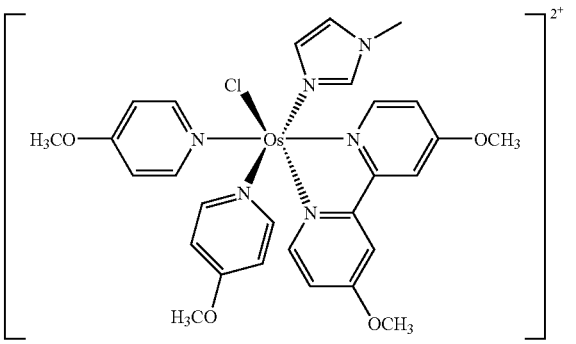<br>"DMO" bis[4,4-dimethoxy-2,2-bypyridine-κN,N'](chloro(3-methylimidazole-κN$^3$)osmium(2+) dichloride | −105 |

TABLE 3

Examples of Low Potential Osmium Mediators and
Known Comparative Mediators and Properties Thereof Under Condition A

| Mediator No. Or Comparative Mediator No. | Structure of Mediator or Comparative Mediator | Redox Potential, $E_{1/2}$ (m/V) versus Ag/AgCl | Linear Slope, k ($\mu C/(mg/dL)$) |
| --- | --- | --- | --- |
| 1 | | −164 | 1.52 |
| 2 | | −168 | 1.49 |
| 3 | | −150 | 1.46 |
| 4 | | −172 | 1.49 |

TABLE 3-continued

| Mediator No. | Structure of Mediator | Redox Potential, $E_{1/2}$ (mV) versus Ag/AgCl | Mediator No. |
|---|---|---|---|
| 11 | (structure shown) | −130 | 1.55 |
| I* | (structure shown) | −110 | 1.14 |
| X* | (structure shown) | −125 | 1.05 |

*These known comparative mediators are disclosed in International Publication No. WO 01/36430 A1 and are merely comparative examples herein.

TABLE 4

Examples of Low Potential Osmium Mediators and
Known Comparative Mediators and Properties Thereof Under Condition B

| Mediator No. Or Comparative Mediator No. | Structure of Mediator or Comparative Mediator | Redox Potential $E_{1/2}$ (m/V) versus Ag/AgCl | Linear Slope, k (μC/(mg/dL)) |
|---|---|---|---|
| 8 | [Os complex structure with imidazole, pyridine, and Cl ligands]$^{2+}$ 2Cl$^-$ | −139 | 1.73 |
| 9 | [Os complex structure with benzimidazole, imidazole, pyridine, and Cl ligands]$^{2+}$ 2Cl$^-$ | −124 | 1.70 |
| X* | [Os complex structure with two OMe-pyridines and imidazole ligands]$^{3+}$ 3Cl$^-$ | −125 | 1.48 |
| XII* | [Os complex structure with pyridyl-imidazole ligands]$^{3+}$ 3Cl$^-$ | −74 | 1.46 |

TABLE 4-continued

Examples of Low Potential Osmium Mediators and
Known Comparative Mediators and Properties Thereof Under Condition B

| Mediator No. Or Comparative Mediator No. | Structure of Mediator or Comparative Mediator | Redox Potential $E_{1/2}$ (m/V) versus Ag/AgCl | Linear Slope, k ($\mu$C/(mg/dL)) |
|---|---|---|---|
| XIII* | 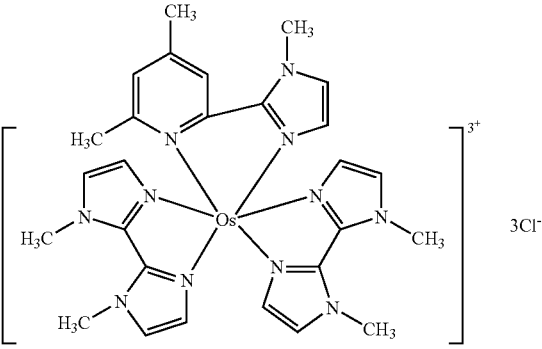 | −97 | 1.52 |

*These known comparative mediators are disclosed in International Publication No. WO 01/36430 A1 and are merely comparative examples herein.

The transition metal complexes of the present invention are well suited for electrochemical sensing applications, given their particular electrochemical properties. For example, as shown above, the redox potentials of the mediators are generally low, such as in a range of from about 0 mV to about −200 mV relative to a Ag/AgCl reference electrode. These redox potentials are particularly desirable for electrochemical sensing applications, being in a range at which the kinetics of the mediators is fast and the electrochemical activity of potentially interfering species is minimized. Mediator Nos. 1-21 thus exemplify electrochemically desirable mediators which are coordination complexes comprising osmium according to the present invention.

The identity of the potentially interfering species just described depends on the particular electrochemical sensing application. Merely by way of example, when the electrochemical sensing application concerns the biofluid, blood, potentially interfering species include ascorbic acid, acetaminophen, and uric acid. Mediator Nos. 1-21 exemplify electrochemically desirable mediators which are coordination complexes comprising osmium that operate at potentials suitable for minimizing the electrochemical activity of such potentially interfering species, while not sacrificing mediator efficiency.

Additionally, the transition metal complexes of the present invention are particularly effective redox mediators in electrochemical sensing applications, given their enhanced ability to collect charge at the working electrode, which in turn enhances the sensitivity of the sensor to the concentration of the analyte being sensed. By way of example, in the general operation of an electrochemical biosensor, such as a glucose sensor, the reduced enzyme, glucose oxidase or glucose dehydrogenase, transfers its electrons to the working electrode via a particular process. In that process, the oxidized form of the redox mediator interacts with the reduced enzyme, thereby receiving an electron and becoming reduced. The reduced mediator travels to the surface of the working electrode, typically by random diffusion, whereupon it transfers the collected electron to the electrode, thereby becoming oxidized.

Ideally, because each glucose molecule loses two electrons in the above-described process, the total amount of electrons or charge collected at the working electrode should be equal to two times the number of glucose molecules oxidized. In practice, however, the total amount of charge collected is almost always less than the ideal or theoretical amount because the electrons may be "lost" during transfer from the enzyme to the electrode. For example, the reduced enzyme may transfer the electrons to oxygen or other chemical species, rather than to the redox mediator. An efficient redox mediator should thus compete favorably for electrons from the enzyme.

Further, ideally, once the redox mediator receives an electron from the enzyme, it should not transfer the electron to another oxidative species, such as oxygen or other chemicals present in the sensor, before being oxidized on the working electrode. A good mediator should thus compete favorably for electrons from the reduced enzyme, as described above, and be substantially chemically inert during its random diffusion to the working electrode whereupon it is oxidized.

An efficient mediator is particularly important in coulometry-based electrochemical biosensing, in which detection of the bioanalyte is based on the total amount of charge collected at the working electrode for a given volume of biofluid. When greater charge is collected at the working electrode, the sensor is advantageously more sensitive. For a coulometry-based glucose sensor, for example, the sensitivity of the sensor may be characterized by the slope value of a linear plot of charge versus glucose concentration as defined by the equation y=kx+b, where y is the collected charge in $\mu$C for a given volume of biofluid, k is the slope in $\mu$C/(mg/dL), x is the glucose concentration in mg/dL, and b is the intercept based on background charge. As demonstrated above, mediators of the present invention that have a negatively charged ligand, such as Mediator Nos. 1-21 that have a chloride ligand, have associated slope values that are significantly higher (for example, about 28% to about 48% higher per Table 3, and about 11% to about 18% higher per Table 4) than those of mediators that have heterocyclic nitrogen-containing ligands surrounding the metal redox center, as exemplified by Comparative Mediator Nos. I, X, XII and XIII.

The above-described data demonstrate favorable properties of transition metal complexes that make these complexes particularly desirable redox mediators. In electrochemical sensing applications, such as the electrochemical sensing of glucose, the transition metal complexes effectively collect electrons from the reduced enzyme and effectively retain the collected electrons prior to delivering them to the working electrode.

As described herein, the transition metal complexes of the present invention are usefully employed as redox mediators in electrochemical sensors. These mediators have very fast kinetics, such that electron exchange between such a mediator and the enzyme and/or the working electrode in the sensor device is rapid, and more particularly, rapid enough to facilitate the transfer of electrons to the working electrode that might otherwise be transferred to another electron scavenger, such as oxygen. The electron-transfer efficiency of a mediator of Formula 1 is enhanced when $L_2$ is a negatively charged ligand, such as a chloride ligand, as demonstrated by the desirable slope values, k, listed above for Mediator Nos. 1-21. By way of comparison, a mediator having a neutral ligand, $L_2$, such as a heterocyclic nitrogen-containing ligand, is less able to transfer electrons from the enzyme to the working electrode, as reflected by the lower slope values listed above for Comparative Mediator Nos. I, X, XII and XIII.

The transition metal complex mediators of the present invention are also quite stable in terms of chemical reactivity with respect to chemical species other than the enzyme and the electrode surface. By way of example, the chemical stability of a mediator of the present invention is such that preferably the predominant, or most preferably the only, reactions in which it participates involves the above-described, electron-transfer reaction between the mediator and the enzyme and the electrochemical redox reaction at the working electrode. This chemical stability may be enhanced when a mediator of Formula 1 wherein $L_2$ is a negatively charged monodentate ligand, has a "bulky" chemical ligand, $L_1$, that spatially or stereochemically shields the redox center, such as $Os2+/3+$, and thereby, reduces undesirable chemical reactivity beyond the fundamentally desired chemical and electrochemical activity. Mediator Nos. 1-21, above, are particular examples of such "bulked", chemically stable mediators of the present invention.

Further by way of example, the thermal and photochemical stability of a mediator of the present invention is preferably such that the mediator is temperature- and light-stable, respectively, under typical use, storage and transportation conditions. For example, mediators of the present invention may be easily handled under normal lighting conditions and may have a shelf life of at least about 18 months at about room temperature, and at least about 2 weeks at about 57° C. Mediator Nos. 1-21, above, are particular examples of such thermally and photochemically stable mediators of the present invention.

Mediators of the claimed sensors have desirable redox potentials in a range at which the electron-transfer kinetics is optimized, or maximized, and the effect of common interfering species present in biofluid is minimized. Mediator Nos. 1-21, above, are particular examples of mediators of suitable redox potential.

The transition metal complex mediators of the present invention also have desirable solubility properties, generally having a solubility of greater than about 0.1 moles/liter at 25° C. for a desired solvent, which is typically an aqueous or a water-miscible solvent. Advantageously, one need only adjust the counter ion or ions, X, of Formula 1, to obtain a desirable solubility for the solvent of choice, be it aqueous or organic.

In summary, the claimed subject matter is directed to enzyme-based electrochemical sensors comprising transition metal complexes with pyridyl-imidazole ligands, which show improved response times in the detection and quantification of fluid analytes. Said transition metal complexes are particularly useful as redox mediators in electrochemical sensing applications. The preferred redox mediators exchange electrons rapidly with enzymes and working electrodes, are stable, are readily synthesized, and have redox potentials that are tailored for the electrooxidation of a variety of analytes, such as those in various biological fluids within the human body. While mediators of the present invention have been described for the most part in terms of glucose sensing, they are useful for the sensing of other analytes, such as lactic acid for example. Generally, if the redox potential of the enzyme used in a particular analyte-sensing application is negative relative to the redox potential of the mediator, the mediator is suitable for that analyte-sensing application. The advantageous properties and characteristics of the transition metal complexes of the present invention make them ideal candidates for use in the electrochemical sensing of glucose, an application of particular importance in the diagnosis and monitoring of diabetes in human populations.

Various aspects and features of the present invention have been explained or described in relation to beliefs or theories, although it will be understood that the invention is not bound to any belief or theory. Further, various modifications, equivalent processes, as well as numerous structures to which the present invention may be applicable will be readily apparent to those of skill in the art to which the present invention is directed upon review of the instant specification. Although the various aspects and features of the present invention have been described with respect to various embodiments and specific examples herein, it will be understood that the invention is entitled to protection within the full scope of the appended claims.

The invention claimed is:
1. A test strip comprising:
a working electrode; and
a counter electrode;
wherein the working electrode comprises:
a transition metal complex having the formula:

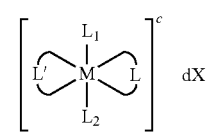

wherein c is a negative, neutral, or positive charge represented by −1 to −5, 0, or +1 to +5, inclusive, respectively;
d is a number of counter ions, X, from 0 to 5, inclusive;
M is cobalt, iron, osmium, ruthenium, or vanadium;
$L_1$ has the formula:

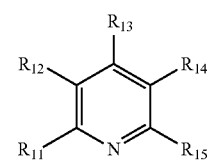

wherein $R_{11}$, $R_{12}$, $R_{14}$ and $R_{15}$ are independently —H, —F, —Cl, —Br, —I, —NO$_2$, —CN, —CO$_2$H, —OH, —NH$_2$, alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl and $R_{13}$ is a C1-C2 alkylamino;

$L_2$ is a negatively charged ligand; and

L and L' are independently:

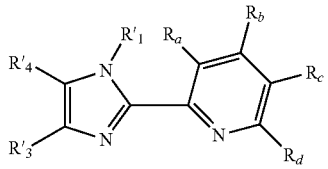

wherein $R'_1$ is a substituted or an unsubstituted alkyl, alkenyl or aryl;

each of $R_a$ and $R_b$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl;

each of $R_c$ and $R_d$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylarninocarbonyl, dialkylaminocarbonyl, alkoxy, alkylamino, dialkylamino, alkanoylarnino, arylcarboxamido, hydrazino, alkylhydrazino, hydroxyfamino, alkoxylarnino, alkylthio, alkenyl, aryl, or alkyl, or a combination of Rc and Rd forms a saturated or an unsaturated 5- or 6-membered ring; and each of $R'_3$ and $R'_4$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl, or a combination of $R'_3$ and $R'_4$ forms a saturated or an unsaturated 5- or 6-membered ring; and a dehydrogenase.

2. The test strip of claim 1, wherein the dehydrogenase is a PQQ-dependent dehydrogenase.

3. The test strip of claim 1, wherein M is osmium.

4. The test strip of claim 1, wherein $R_{13}$ is a C1 alkylamino.

5. A test strip comprising:

a working electrode; and a counter electrode;

wherein the working electrode comprises:

a transition metal complex having the formula:

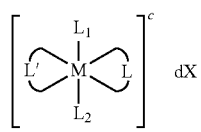

wherein c is a negative, neutral, or positive charge represented by −1 to −5, 0, or +1 to +5, inclusive, respectively;

d is a number of counter ions, X, from 0 to 5, inclusive;

M is cobalt, iron, osmium, ruthenium, or vanadium;

$L_1$ has the formula:

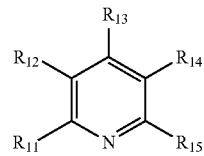

wherein $R_{11}$, $R_{12}$, $R_{14}$ and $R_{15}$ are independently —H, —F, —Cl, —Br, —I, —NO$_2$, —CN, —CO$_2$H, —OH, —NH$_2$, alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl and $R_{13}$ is a C1-C2 alkoxy;

$L_2$ is a negatively charged ligand; and

L and L' are independently:

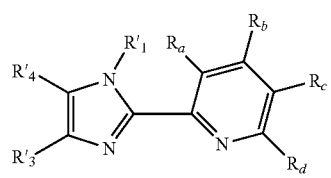

wherein $R'_1$ is a substituted or an unsubstituted alkyl, alkenyl or aryl;

each of $R_a$ and $R_b$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl;

each of $R_c$ and $R_d$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylarninocarbonyl, dialkylaminocarbonyl, alkoxy, alkylamino, dialkylamino, alkanoylarnino, arylcarboxamido, hydrazino, alkylhydrazino, hydroxyfamino, alkoxylarnino, alkylthio, alkenyl, aryl, or alkyl, or a combination of Rc and Rd forms a saturated or an unsaturated 5- or 6-membered ring; and each of $R'_3$ and $R'_4$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl, or a combination of $R'_3$ and $R'_4$ forms a saturated or an unsaturated 5- or 6-membered ring; and a dehydrogenase.

6. The test strip of claim 5, wherein the dehydrogenase is a PQQ-dependent dehydrogenase.

7. The test strip of claim 5, wherein M is osmium.

8. The test strip of claim 5, wherein $R_{13}$ is a C1 alkoxy.

9. A method for monitoring the concentration of an analyte in a biological fluid, the method comprising:

applying a sample containing the analyte to an electrochemical sensor, the electrochemical sensor comprising:

a working electrode, wherein the working electrode comprises a transition metal complex having the formula:

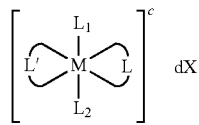

wherein c is a negative, neutral, or positive charge represented by −1 to −5, 0, or +1 to +5, inclusive, respectively;
d is a number of counter ions, X, from 0 to 5, inclusive;
M is cobalt, iron, osmium, ruthenium, or vanadium;
$L_1$ has the formula:

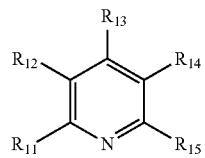

wherein $R_{11}$, $R_{12}$, $R_{14}$ and $R_{15}$ are independently —H, —F, —Cl, —Br, —I, —NO$_2$, —CN, —CO$_2$H, —OH, —NH$_2$, alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl and $R_{13}$ is a C1-C2 alkylamino;
$L_2$ is a negatively charged ligand; and
L and L' are independently:

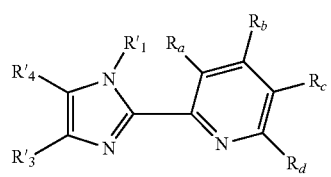

wherein $R'_1$ is a substituted or an unsubstituted alkyl, alkenyl or aryl;
each of $R_a$ and $R_b$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl;
each of $R_c$ and $R_d$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl, or a combination of Rc and Rd forms a saturated or an unsaturated 5- or 6-membered ring; and each of $R'_3$ and $R'_4$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl, or a combination of $R'_3$ and $R'_4$ forms a saturated or an unsaturated 5- or 6-membered ring; and a dehydrogenase; and a counter electrode; and determining the concentration of an analyte in the sample.

10. The method of claim 9, wherein the dehydrogenase is a PQQ-dependent dehydrogenase.

11. The method of claim 9, wherein the analyte is glucose.

12. The method of claim 9, wherein $R_{13}$ is a C1 alkylamino.

13. A method for monitoring the concentration of an analyte in a biological fluid, the method comprising:

applying a sample containing the analyte to an electrochemical sensor, the electrochemical sensor comprising:

a working electrode, wherein the working electrode comprises a transition metal complex having the formula:

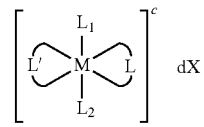

wherein c is a negative, neutral, or positive charge represented by −1 to −5, 0, or +1 to +5, inclusive, respectively;
d is a number of counter ions, X, from 0 to 5, inclusive;
M is cobalt, iron, osmium, ruthenium, or vanadium;
$L_1$ has the formula:

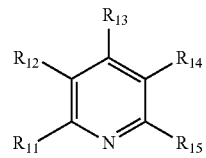

wherein $R_{11}$, $R_{12}$, $R_{14}$ and $R_{15}$ are independently —H, —F, —Cl, —Br, —I, —NO$_2$, —CN, —CO$_2$H, —OH, —NH$_2$, alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl and $R_{13}$ is a C1-C2 alkoxy;

$L_2$ is a negatively charged ligand; and

L and L' are independently:

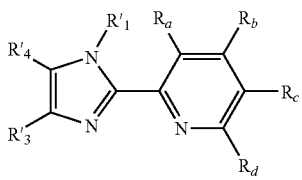

wherein $R'_1$ is a substituted or an unsubstituted alkyl, alkenyl or aryl;

each of $R_a$ and $R_b$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl;

each of $R_c$ and $R_d$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl, or a combination of Rc and Rd forms a saturated or an unsaturated 5- or 6-membered ring; and each of $R'_3$ and $R'_4$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl, or a combination of $R'_3$ and $R'_4$ forms a saturated or an unsaturated 5- or 6-membered ring; and a dehydrogenase; and a counter electrode; and determining the concentration of an analyte in the sample.

14. The method of claim 13, wherein the dehydrogenase is a PQQ-dependent dehydrogenase.

15. The method of claim 13, wherein the analyte is glucose.

16. The method of claim 13, wherein $R_{13}$ is a C1 alkoxy.

* * * * *